US011524181B2

(12) United States Patent
Ciresianu et al.

(10) Patent No.: US 11,524,181 B2
(45) Date of Patent: Dec. 13, 2022

(54) INTRAOPERATIVE RADIATION THERAPY SYSTEM

(71) Applicant: BEST THERATRONICS LTD., Ottawa (CA)

(72) Inventors: Andrei M. Ciresianu, Ottawa (CA); Shawn Luimes, Spencerville (CA); Christopher A. Jechel, Perth (CA)

(73) Assignee: Best Theratronics Ltd., Ottawa (CA)

( * ) Notice: Subject to any disclaimer, the term of this patent is extended or adjusted under 35 U.S.C. 154(b) by 690 days.

(21) Appl. No.: 16/381,263

(22) Filed: Apr. 11, 2019

(65) Prior Publication Data

US 2019/0314645 A1    Oct. 17, 2019

Related U.S. Application Data

(60) Provisional application No. 62/659,132, filed on Apr. 17, 2018.

(51) Int. Cl.
*A61N 5/10* (2006.01)

(52) U.S. Cl.
CPC ......... *A61N 5/1083* (2013.01); *A61N 5/1082* (2013.01); *A61N 2005/1089* (2013.01)

(58) Field of Classification Search
CPC ...... A61N 5/10; A61N 5/1083; A61N 5/1082; A61N 5/1001; A61N 5/1077; A61N 2005/1074
See application file for complete search history.

(56) References Cited

U.S. PATENT DOCUMENTS

| | | | | |
|---|---|---|---|---|
| 3,030,639 A | * | 4/1962 | Boyer | A47B 23/02 5/651 |
| 5,298,905 A | * | 3/1994 | Dahl | G01S 7/34 342/118 |

(Continued)

FOREIGN PATENT DOCUMENTS

| | | | | |
|---|---|---|---|---|
| CN | 107174753 A | * | 9/2017 | ........... A61N 5/1015 |
| EP | 1815950 A1 | | 8/2007 | |

(Continued)

OTHER PUBLICATIONS

Extended EPO Search Report in corresponding EPO Application No. 19788346.5, dated May 19, 2021, 9 pages.

(Continued)

*Primary Examiner* — Thaddeus B Cox
*Assistant Examiner* — Marc D. Honrath

(57) ABSTRACT

The IORT system includes a moveable cart, a robot arm assembly coupled to the cart, at least one applicator fixed relative to a patient, a treatment head coupled to the robot arm assembly for selective alignment with the applicator in a soft-docking procedure, and a haptic control assembly on the treatment head. A plurality of arm members is pivotally coupled to each other to provide at least five axes of movement for increased positioning flexibility and the enhanced flexibility increases the reach of the treatment head for accurate alignment. The alignment follows a two-stage process with a coarse alignment performed by the haptic control assembly to position a sensor array on the treatment head within detection range of an endcap on the applicator. Final alignment is autonomous employing range data from the sensor array to accurately position the treatment head with respect to the applicator.

35 Claims, 17 Drawing Sheets

(56) References Cited

U.S. PATENT DOCUMENTS

| | | | |
|---|---|---|---|
| 5,321,271 | A | 6/1994 | Schonberg et al. |
| 6,078,036 | A | 6/2000 | Cook et al. |
| 8,269,197 | B2 | 9/2012 | Goer et al. |
| 8,506,555 | B2 | 8/2013 | Morales |
| 8,588,368 | B2 | 11/2013 | Fantini et al. |
| 9,040,945 | B1 | 5/2015 | Hayman |
| 9,126,036 | B2 | 9/2015 | Leek |
| 9,737,371 | B2 | 8/2017 | Romo et al. |
| 9,999,787 | B1 * | 6/2018 | Ruohonen ............ A61N 5/1047 |
| 11,110,302 | B2 * | 9/2021 | Dai ...................... A61N 5/1049 |
| 2009/0024142 | A1 * | 1/2009 | Ruiz Morales .......... B25J 9/041 606/130 |
| 2011/0017920 | A1 | 1/2011 | Goer et al. |
| 2012/0035462 | A1 * | 2/2012 | Maurer, Jr. .......... A61N 5/1077 600/411 |
| 2016/0184032 | A1 * | 6/2016 | Romo ................... B25J 9/1682 606/130 |
| 2017/0151021 | A1 | 6/2017 | Quaid, III |
| 2017/0340902 | A1 | 11/2017 | Vilsmeier et al. |
| 2018/0015303 | A1 | 1/2018 | Fishman |
| 2020/0054896 | A1 * | 2/2020 | Johnson ................ A61N 5/1065 |
| 2020/0253678 | A1 * | 8/2020 | Hulford ................ A61B 34/37 |

FOREIGN PATENT DOCUMENTS

| | | |
|---|---|---|
| WO | WO03077101 A2 | 9/2003 |
| WO | WO2016054256 | 4/2016 |
| WO | WO2016054256 A1 | 4/2016 |

OTHER PUBLICATIONS

PCT/CA2019/050470, International Search Report and Written Opinion of The International Searching Authority, dated Jun. 18, 2019, 9 pages.

India Examination Report, dated Oct. 12, 2021, issued in corresponding India Patent Application No. 202027048617, 5 pages.

* cited by examiner

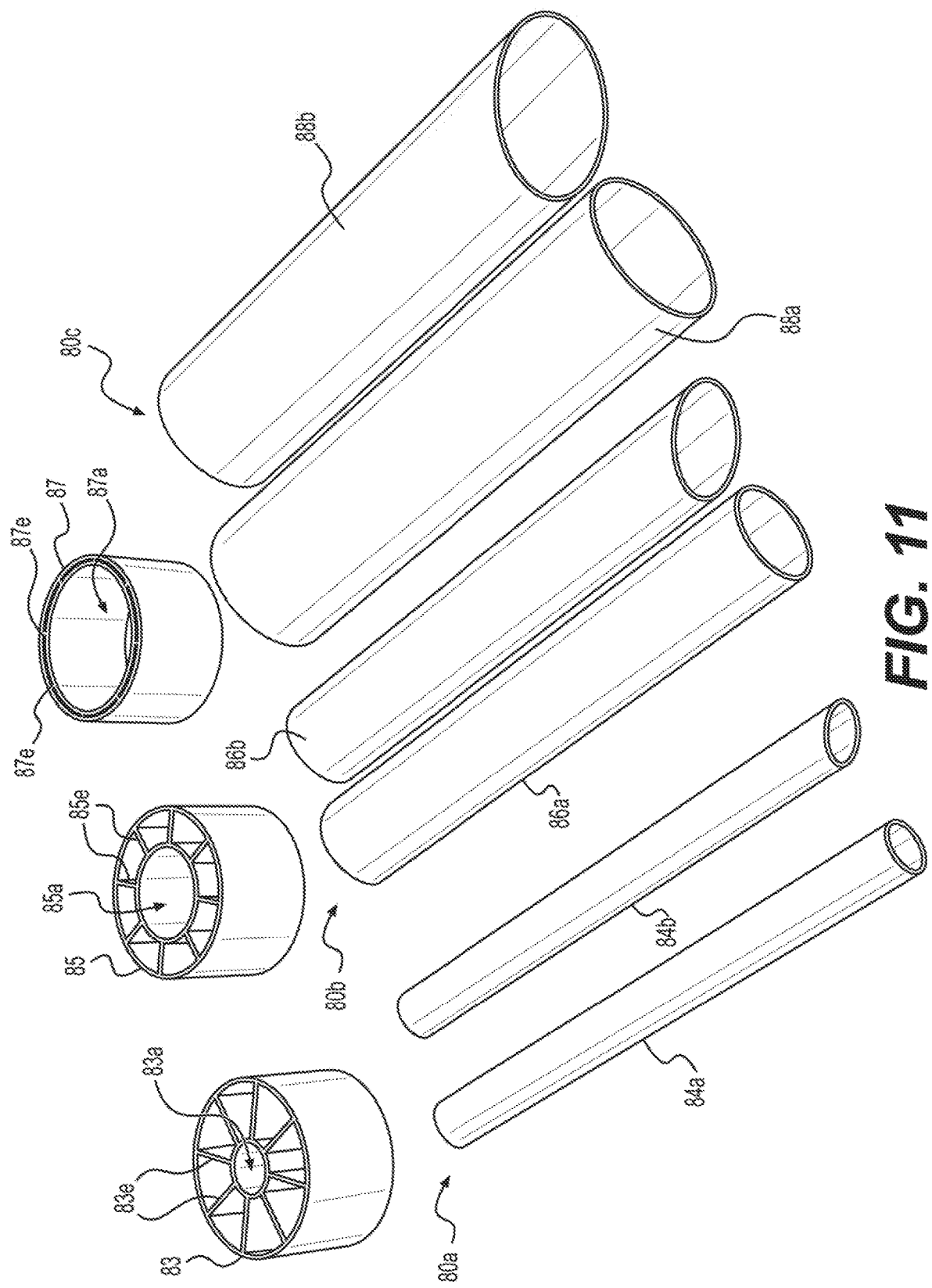

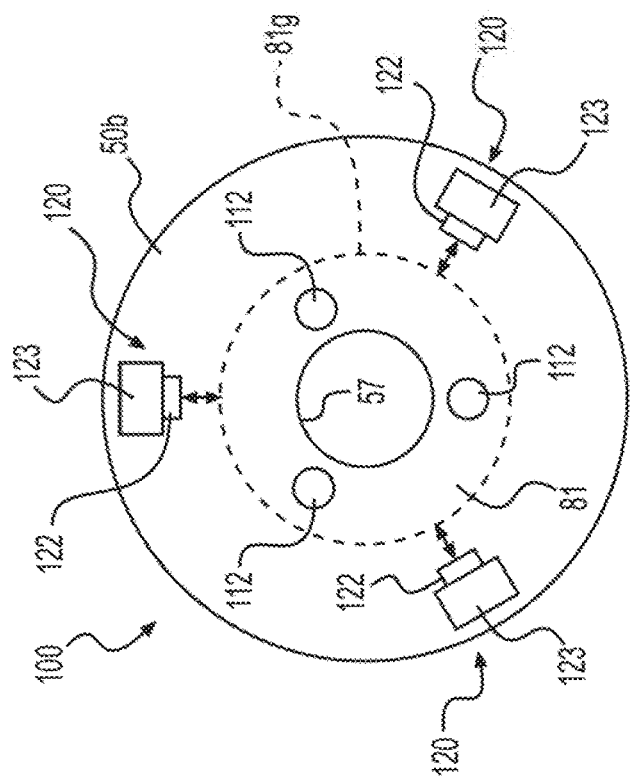
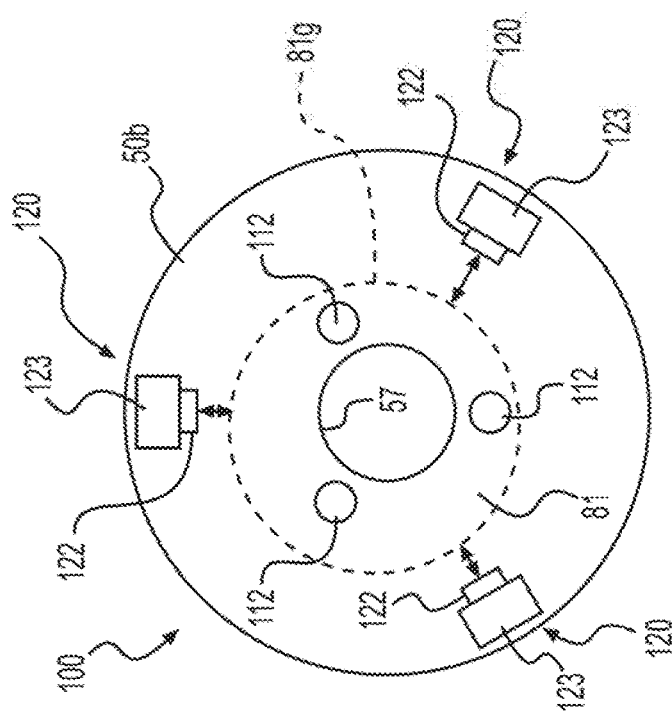

INTRAOPERATIVE RADIATION THERAPY SYSTEM

CROSS REFERENCE TO RELATED APPLICATION

This application claims priority under 35 U.S.C. § 119 to U.S. Provisional Patent Application No. 62/659,132, filed on Apr. 17, 2018, hereby incorporated herein by reference in its entirety.

FIELD OF THE INVENTION

The present invention relates generally to radiation therapy systems, and particularly to an intraoperative radiation therapy system with haptic control and integrated automatic alignment of a treatment head to an electron applicator.

DESCRIPTION OF THE RELATED ART

Certain unfortunate cancer patients may have to undergo surgery as part of their treatment, especially for removal of a cancerous tumor. The procedure may be a straightforward excising of the tumor, or it may also require radiation therapy to ensure eradication of any residual disease. In the case of the latter, an intraoperative radiation therapy (IORT) machine or device is used to treat the target area.

Many different IORT devices exist to facilitate radiation therapy and generally fall into two categories, an immobile IORT device and a mobile IORT device. The immobile IORT device is typically housed within a shielded bunker in a medical facility, which provides the necessary high energy electron beams for the treatment. Electron beams in the megaelectron-volt (MeV) energy range are the most common form of radiation used for such treatments, another example of which is X-rays. While effective in its own way, the design poses a potential risk to the patient because the patient must be moved from the operating room (OR) to the location of the immobile IORT device. Transport of a patient mid-surgery poses risks to the patient such as potential infection moving from a sterile environment to a non-sterile environment and extended time under anesthesia.

Time is a critical factor for any surgery, both in terms of the health and safety of the patient as well as expenses. Like most complex medical devices, IORT machines are expensive capital equipment for a medical facility, and in the case of immobile IORT devices, are usually underutilized in view of set up time needed for a treatment. The logistics of the operation for moving the anaesthetized patient and the required time for setup takes a large portion of the scheduled operation while the radiation treatment itself is only a fraction. Therefore, the number of patients that can be treated within a given period of time by the immobile IORT device is greatly reduced.

Mobile IORT devices, on the other hand, eliminate many of the time constraints posed by their immobile versions. However, most conventional mobile IORT machines may require increased time for setup or adjustments due to the design of the machine. For example, some current examples of mobile IORT machines include a treatment head mounted to a gantry or a simplified robot arm, which provides limited movement for positioning of the treatment head. The limited mobility increases the time for setup or increases the difficulty for positioning the treatment head relative to a certain target area of the patient's body.

In light of the above, there is still a need in the medical arts for an IORT device or system that can deliver efficient radiotherapy with minimal setup time. Thus, an intraoperative radiation therapy system with haptic control and integrated alignment of a treatment head and electron applicator solving the aforementioned problems is desired.

SUMMARY OF THE INVENTION

The IORT system includes a moveable cart, a robot arm assembly coupled to the cart, at least one applicator fixed relative to a patient, a treatment head coupled to the robot arm assembly for selective alignment with the applicator in a soft-docking procedure, and a haptic control assembly on the treatment head. A plurality of arm members is pivotally coupled to each other to provide at least five axes of movement for increased positioning flexibility. The treatment head is attached to at least one distal arm, and the enhanced flexibility increases the reach of the treatment head for accurate alignment. The alignment follows a two-stage process with a coarse alignment performed by the haptic control assembly to position a sensor array on the treatment head within detection range of an endcap on the applicator. Final alignment is autonomous employing range data from the sensor array to accurately position the treatment head with respect to the applicator.

These and other features of the present invention will become readily apparent upon further review of the following specification and drawings.

BRIEF DESCRIPTION OF THE DRAWINGS

FIG. 11 is a perspective view of various applicators used in the IORT system shown in FIGS. 1A and 1B.

FIG. 13A is a schematic diagram of a second sensor set on the sensor array in the IORT system shown in FIGS. 1A and 1B, the second sensor set detecting a misaligned position of an outer surface of the endcap after coarse alignment.

FIG. 13B is a schematic diagram of the second sensor set on the sensor array shown in FIG. 13A, the second sensor set being in an aligned position relative to the outer surface of the endcap after adjusting position from FIG. 13A.

Similar reference characters denote corresponding features consistently throughout the attached drawings.

DETAILED DESCRIPTION OF THE PREFERRED EMBODIMENTS

Figure 1A:
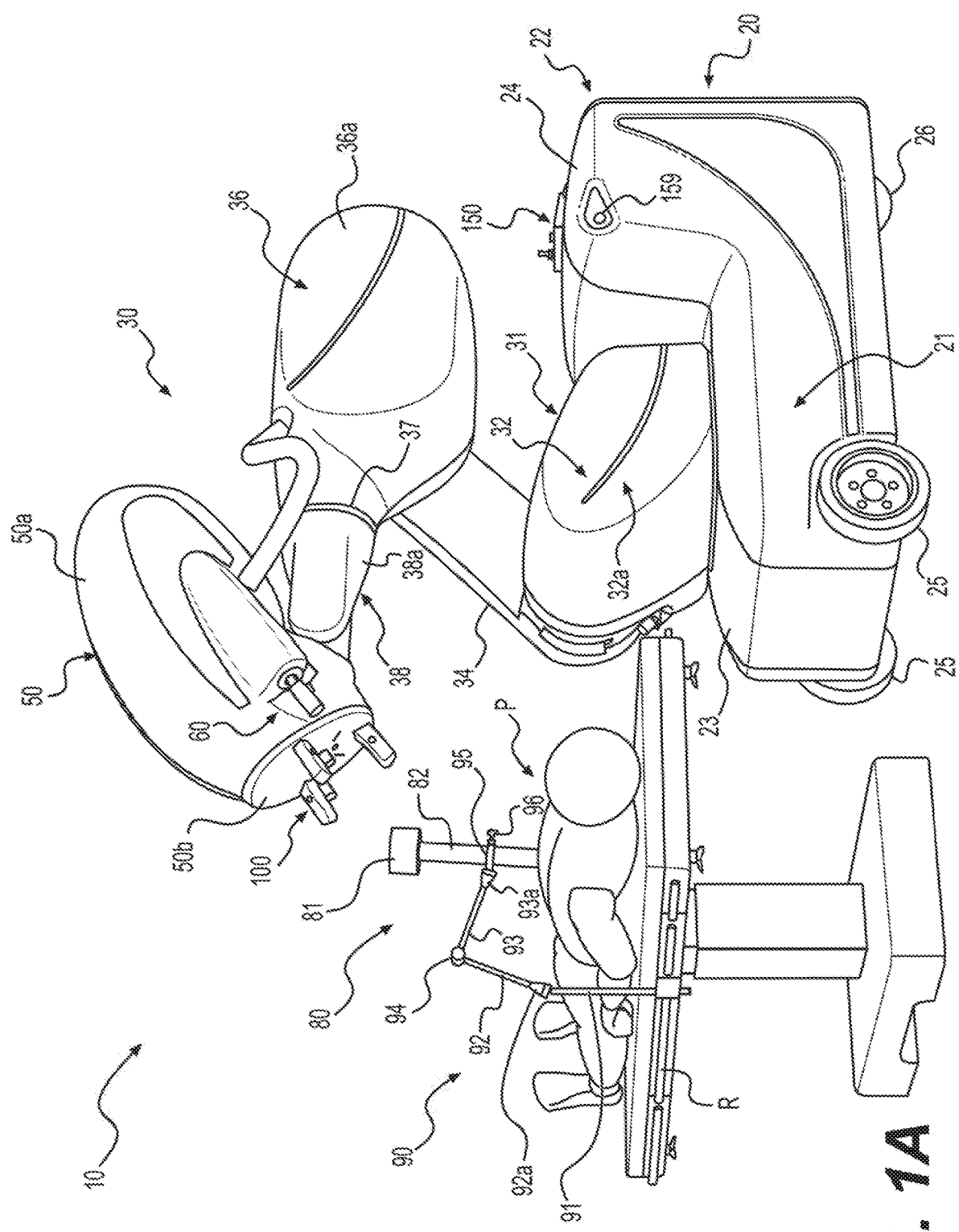
FIG. 1A is an environmental, perspective view of an IORT system according to the present invention with a treatment head of a robot arm assembly in an approach position relative to an applicator.
Figure 1B:
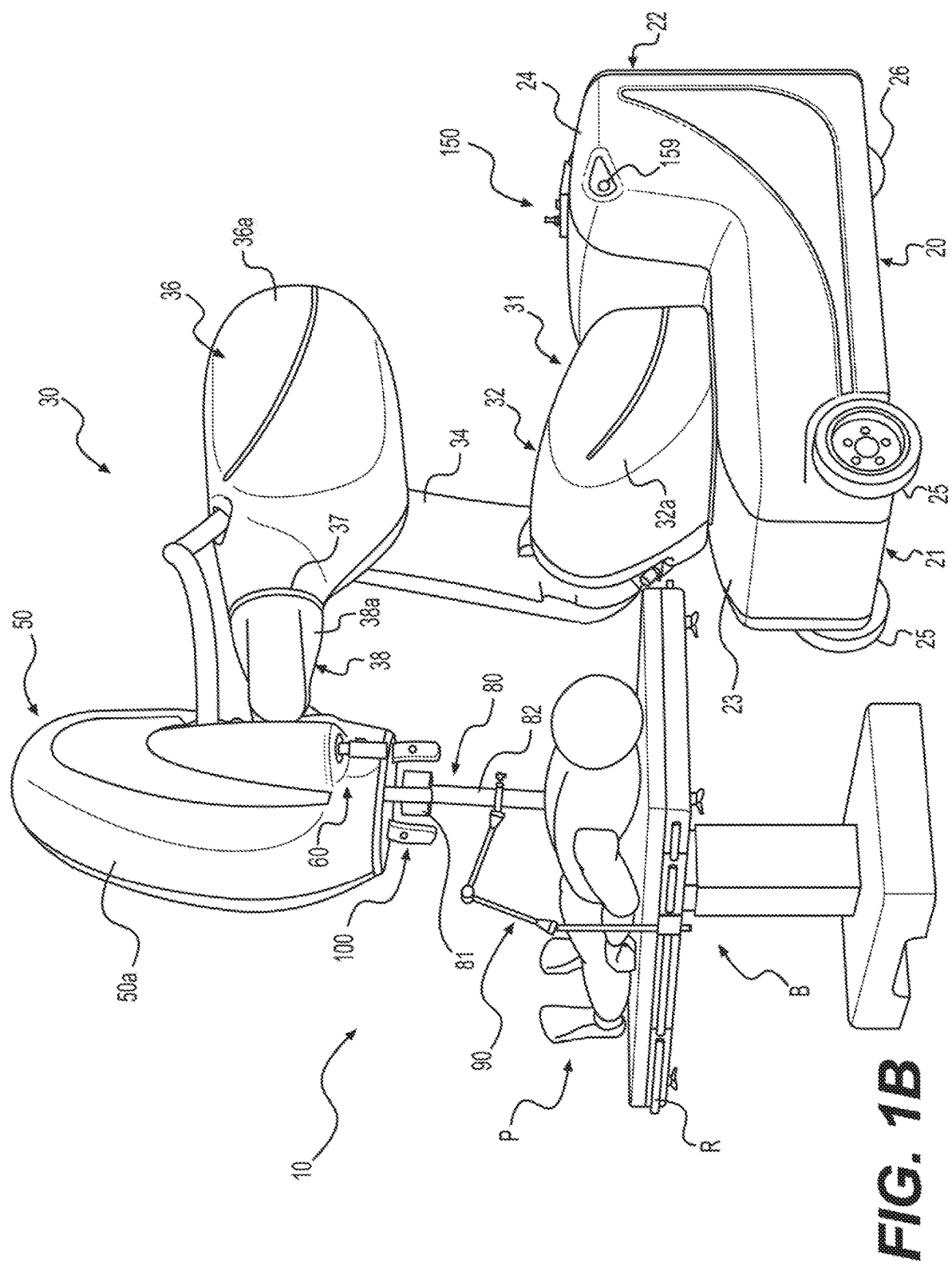
FIG. 1B is an environmental, perspective view of the IORT system shown in FIG. 1A with the treatment head aligned with the applicator.

The IORT system, generally referred to by the reference number 10 in the drawings, provides a mobile, easily maneuverable, soft-docking, radiation treatment device and system that can be quickly positioned and accurately aligned for subsequent treatment. As shown in FIGS. 1A and 1B, the IORT system 10 includes a movable cart or carriage 20 for positioning the IORT system 10 near a patient P, an articulating robot arm assembly 30 mounted to the cart 20, a treatment head 50 coupled to the robot arm assembly 30, and an applicator 80 fixed in position near a target area on the patient P.

The cart 20 can be a generally blocky L-shaped vehicle, when seen from the side, having one or more wheels 25, 26 mounted near the bottom of the cart 20 with at least one of the wheels being steerable to maneuver the cart 20. As best seen in FIGS. 1A and 1B, the cart 20 is provided with a pair of front wheels 25 and one or more rear wheels 26 spaced from the front wheels 25. The rear wheel or wheels 26 are not clearly seen in the drawings due to their relatively close spacing. The cart 20 desirably has an overall length of about 1700 mm with a wheelbase, i.e. the distance between the axles of the front wheels 25 and the rear wheel 26, of about 1300 mm. The width of the cart 20 is about 1000 mm. The general L-shape of the cart 20 divides the cart 20 into a short front section 21 and a tall rear section 22, where the front section 21 forms a front shelf or bed 23 relative to the tall rear section 22 of the cart 20 for rotatably supporting the robot arm assembly 30 thereon. The rear section 22 also forms a rear shelf or bed 24, and the rear shelf 24 enables fixed or detachable mounting of a control panel 150 thereon. Exemplary height dimensions are about 620 mm for the front shelf 23 and about 860 mm for the rear shelf 24 with respect to ground. It is to be understood that all of these dimensions can be varied depending on the application by the user and any given medical facility constraints or standards in terms of available dimensions for transport of medical equipment within the facility.

Figure 2:
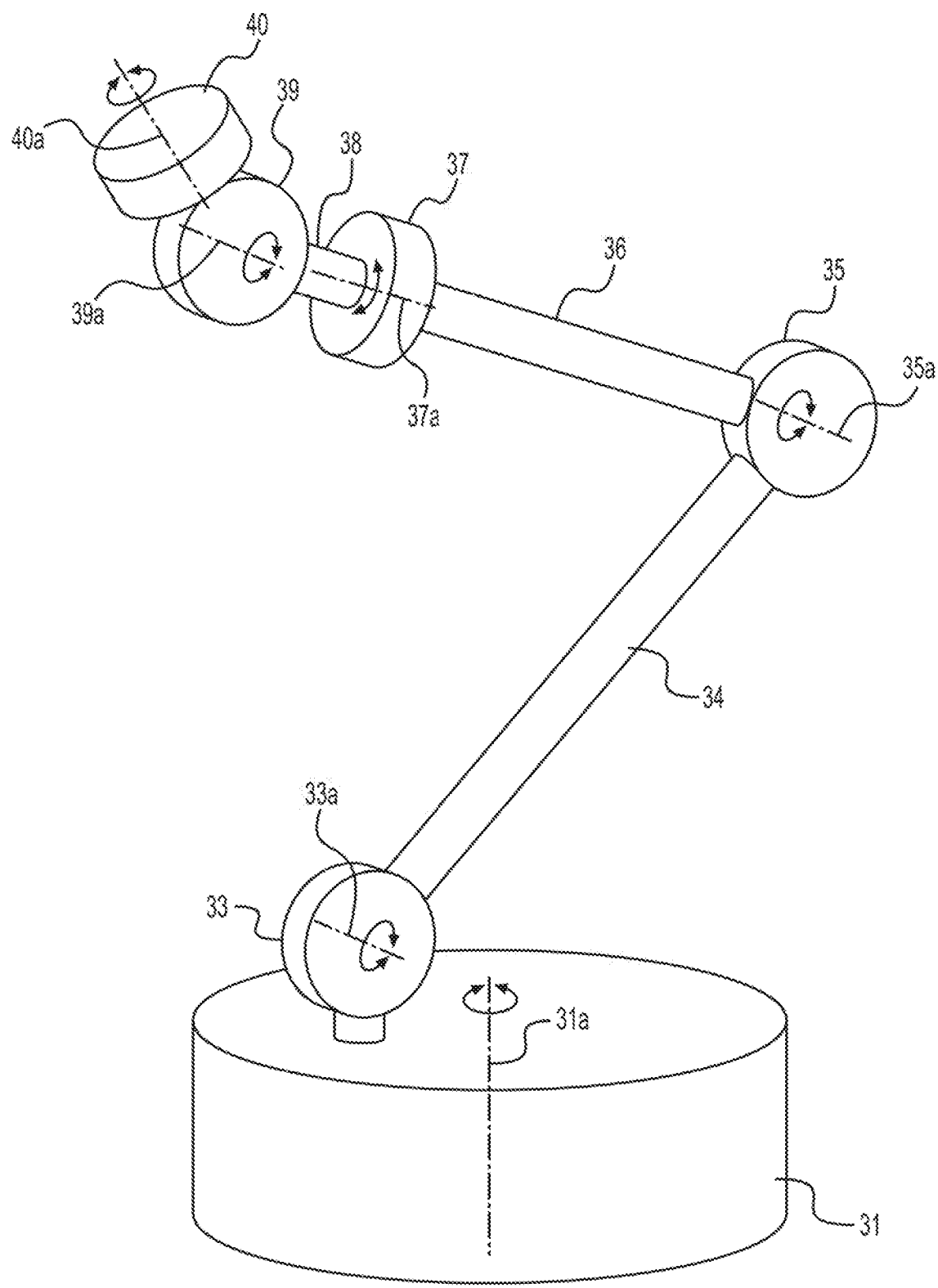
FIG. 2 is a schematic diagram of a robot arm assembly in the IORT system shown in FIGS. 1A and 1B with elongate bars representing specific robot arm members and disks representing specific joints.
Figure 3:
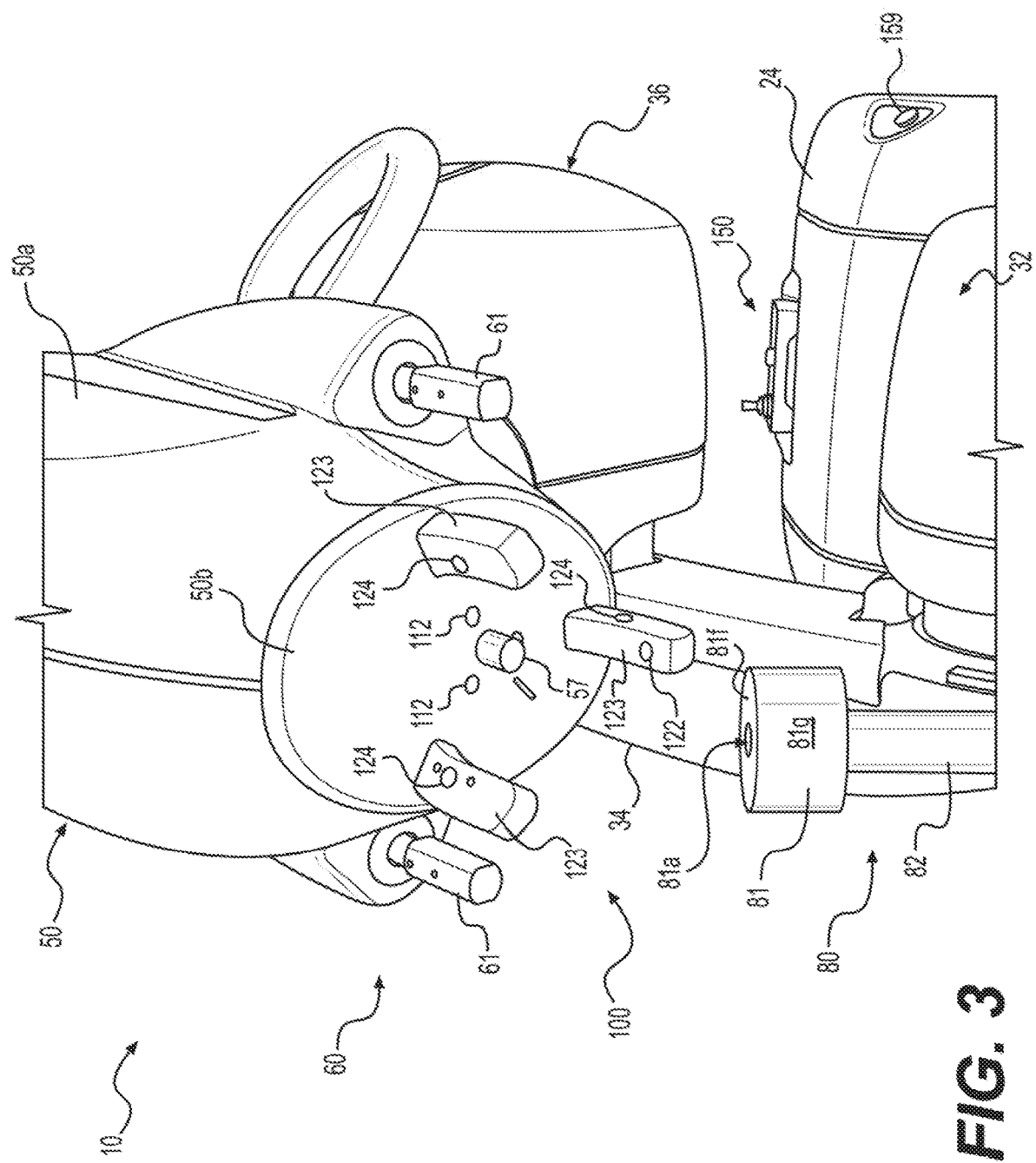
FIG. 3 is a front, detailed perspective view of the treatment head in the IORT system shown in FIGS. 1A and 1B at a coarse approach position relative to the applicator.
Figure 4:
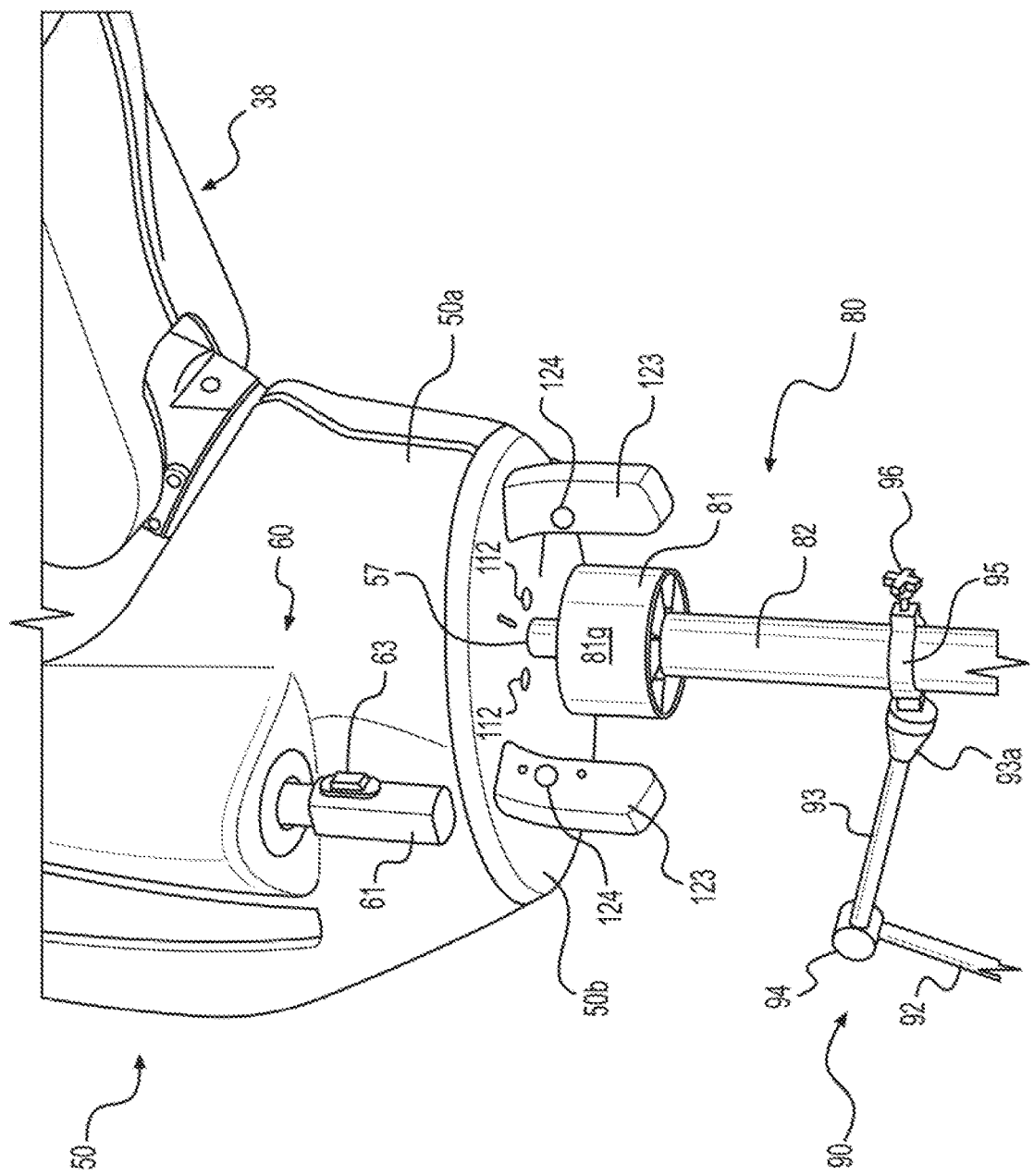
FIG. 4 is a side, detailed perspective view of the treatment head in the IORT system shown in FIGS. 1A and 1B at an aligned position relative to the applicator.

As best shown in FIGS. 1A, 1B, and 2-5, the robot arm assembly 30 includes a treatment head 50 that must be accurately positioned with respect to an applicator 80 mounted near the treatment target area of the patient P in a soft-docking process. It is noted that the schematic diagram of FIG. 2 depicts specific arm members as elongate bars or beams and specific joints as cylindrical disks unless otherwise described. In general, the treatment head 50 generates and emits X-rays or other types of radiation used in radiotherapy while the applicator 80 collimates these emissions to the target area. Thus, accurate alignment between the treatment head 50 and the applicator 80 during setup is critical for efficient treatment in a soft-docking process. Otherwise, misalignments can potentially cause irradiation of undesirable regions, insufficient radiation dosage on the target area, and/or present unintended radioactive hazards to the patient and others within the affected area.

To enable accurate positioning of the treatment head 50, the robot arm assembly 30 is configured for expanded maneuverability compared to most conventional IORT devices and includes a sensor array 100. The robot arm assembly 30 includes a rotary base or turntable 31 coupled either on the front shelf 23 or inside the front section 21. The turntable 31 enables the robot arm assembly 30 to rotate about a vertical, first axis 31a during the positioning process. In an embodiment, a radial section 32 extends at an angle from the base of the turntable 31 so as to provide a first pivot joint 33 at a distal end offset from the first axis 31a. This first pivot joint 33 can be placed anywhere about the turntable 31, even along the first axis 31a. However, the offset position is desired so as to provide room for the robot arm assembly 30 to fold into a relative compact form on the cart 20, e.g., for transport, and unfold during active positioning. The folded and unfolded states can be ascertained from comparing the intermediate unfolded states shown in FIGS. 1A and 1B. The first pivot joint 33 defines a horizontal, second axis 33a orthogonal to the first axis 31a.

One end of an elongate, first arm member 34 is pivotably coupled to the first pivot joint 33 of the radial section 32 and rotatable about the second axis 33a. The opposite end of the first arm member 34 includes a second pivot joint 35 defining a third axis 35a spaced and parallel to the second axis 33a. An elongate, second arm member 36 is pivotably coupled to the second pivot joint 35 at one end and rotatable about the third axis 35a. This pivoting connection between the first arm member 34 and the second arm member 36 facilitates selective folding and unfolding of the robot arm assembly 30 within a vertical plane, which respectively lowers and raises the attached treatment head 50. In an embodiment, the first arm member 34 is about 770 mm in length.

The opposite end of the second arm member 36 includes a third pivot joint 37 that pivotably couples one end of an elongate, third arm member 38 to the second arm member 36. The third arm member 38 can also be referred to as a neck. Unlike the first pivot joint 33 and the second pivot joint 35, the third pivot joint 37 defines a fourth axis 37a that is orthogonal to the second and third axes 33a, 35a and coaxial with the second arm member 36. The treatment head 50 is coupled to the opposite end of the third arm member 38, the third arm member 38 being a distal arm member of the robot arm assembly 30. The third pivot joint 37 enables the attached treatment head 50 to oscillate about the fourth axis 37a relative to the second arm member 36 much in the same manner as a person's wrist joint where the hand can rotate at the wrist joint relative to the forearm. As such, the third pivot joint 37 can also be referred to as a wrist. In an embodiment, the overall length of the second arm member 36 and the third arm member 38 is about 780 mm, the overall length being due to both arm members 36, 38 moving together without any change in individual lengths though each is pivotal about different axes.

Further manipulation of the treatment head 50 is provided by a combination joint assembly at the opposite end of the third arm member 38. As best seen in FIG. 2, the distal or opposite end of the third arm member 38 includes a fourth pivot joint 39 defining a fifth axis 39*a*, this axis being orthogonal to the fourth axis 37*a*. The fourth pivot joint 39 permits the treatment head 50 to pitch forward and backward about the fifth axis 39*a* relative to the third arm member 38.

A fifth pivot joint 40 is operably coupled to the fourth pivot joint 39, e.g., by a connected linkage, and defines a sixth pivot axis 40*a* orthogonal to the fifth pivot axis 39*a*. Similar to the third pivot joint 37, the fifth pivot joint 40 enables the treatment head 50 to oscillate about the sixth pivot axis 40*a*, but this movement is relative to the fourth pivot joint 39. Though the fourth pivot axis 37*a* and the sixth pivot axis 40*a* are generally the same, especially when both axes coincide, situations may arise during use where further movement along that general axis is required for accurate alignment, an example of which is shown in FIG. 2. In FIG. 2, one can see the fifth pivot joint 40 pitched upward relative to the third arm member 38 such that the sixth axis 40*a* intersects the fourth axis 37*a* at an angle, which places an output or working end 50*b* of the attached treatment head 50 at a higher elevation relative to the fourth axis 37*a*.

It can be seen from the above description that the robot arm assembly 30 can move about at least five different axes, more specifically six different axes, compared to most conventional IORT robot systems which may contain only four or less. This configuration provides a spherical region of space about the vertical, first axis 31*a* that can be reached by the treatment head 50 limited by the full extension of the robot arm assembly 30 and enhances the positioning capacity and flexibility of the attached treatment head 50 so as to enable treatment of target areas that may be difficult to reach for conventional robots. During use with the cart 20 parked at a preselected position near the patient P, the turntable 31 horizontally positions the treatment head 50 relative to the cart 20 by rotating about the first axis 31*a*. Subsequent or congruent pivoting/rotating movements of the first arm member 34 and the second arm member 36 about the second axis 33*a* and the third axis 35*a* raises or lowers the treatment head 50 relative to the patient P and the applicator 80, the applicator 80 being fixed in position near the patient P. Fine positional adjustments of the treatment head 50 are facilitated by the third arm member 38 rotating about the fourth axis 37*a* and pivoting/rotating movements of the fourth joint 39, the fifth joint 40, or a combination of both fourth and fifth joints 39, 40.

Each of the above joints 33, 35, 37, 39, 40 and the turntable 31 is desirably powered by corresponding servomotors (not shown) for consistency, accuracy, and ease of control in their movements. Other types of motors such as stepper motors, fluid motors, and the like can also be used as long as the traversal speed of the connected member or members can be suitably controlled. The gearing for the joints 33, 35, 37, 39, 40 is desirably configured to move the corresponding member in a relatively slow yet controlled manner. This provides a measure of safety during operation so as to prevent any potential injury, harm, or accident to the user/operator, the patient P, any nearby members of the operating team, and/or nearby equipment that can be caused by unintentional rapid movements of the robot arm assembly 30. It is also noted that the drawings show the robot arm assembly 30 with ovoid or oval-shaped covers 32*a*, 36*a*, especially on the radial section 32 of the turntable 31 and the second arm member 36. These covers 32*a*, 36*a* house and protect the working components schematically shown in FIG. 2 therein. It is to be understood that a variety of shapes for the covers can be used as long as they retain the protective and housing aspects of the covers without hindering the movements of the arm members. Other covers such as a cover 38*a* for the third arm member 38 or even a cover for the second arm member 34 can also be provided.

Referring to FIGS. 1A, 1B, and 2-6, the treatment head 50 includes an ovoid cover 50*a* for housing and protecting components therein. The treatment head 50 generally contains a linear accelerator that uses radio frequency (RF) power to accelerate a beam of electrons EB to high energies, i.e., in the megaelectron-volt range. This high energy electron beam EB imparted to the patient's body provides the therapeutic action of radiation therapy.

Figure 6:
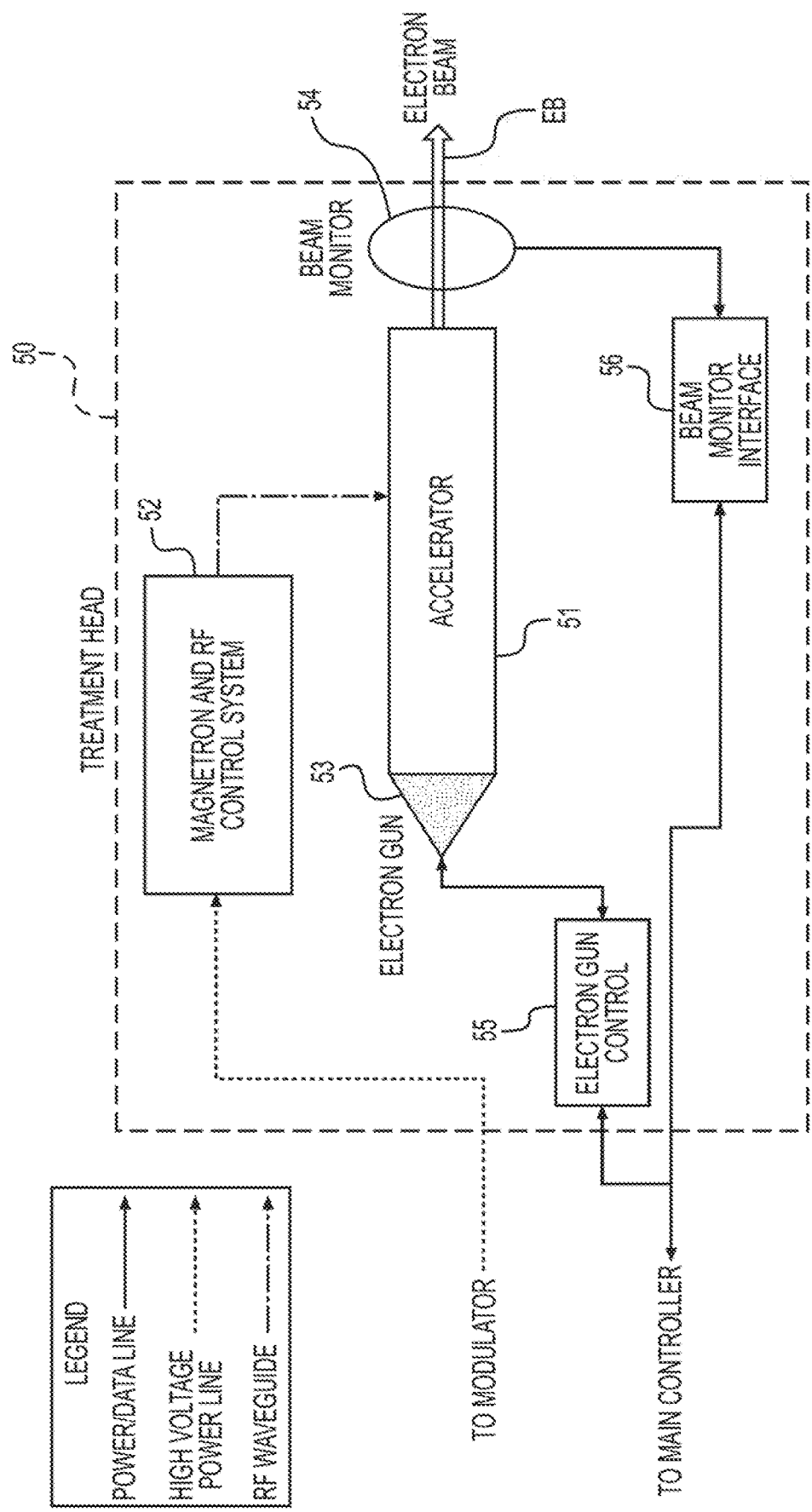
FIG. 6 is a block diagram of the treatment head in the IORT system shown in FIGS. 1A and 1B.
Figure 7:
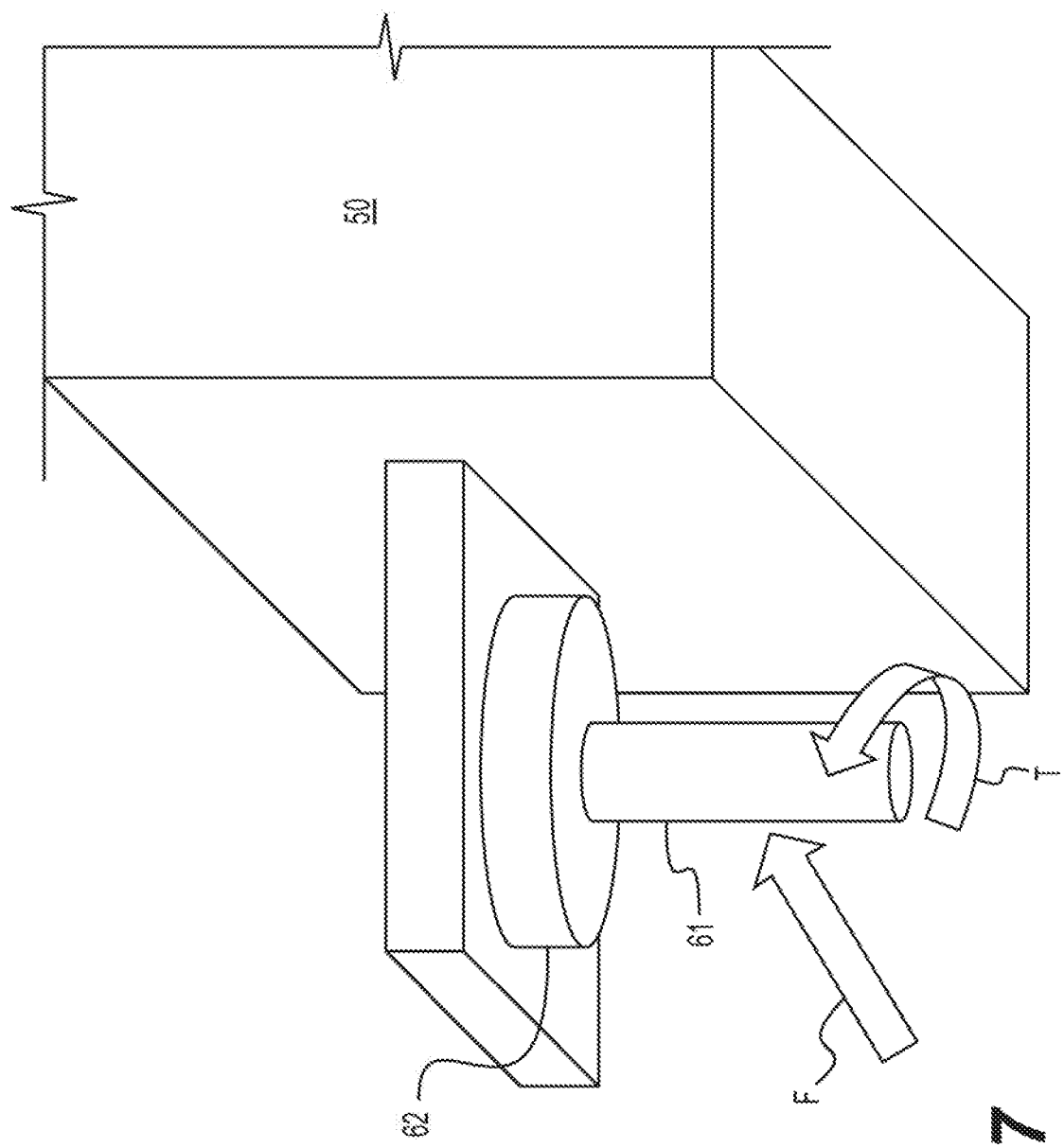
FIG. 7 is a schematic perspective view of a haptic control assembly on the treatment head shown in FIGS. 1A and 1B.
Figure 8:
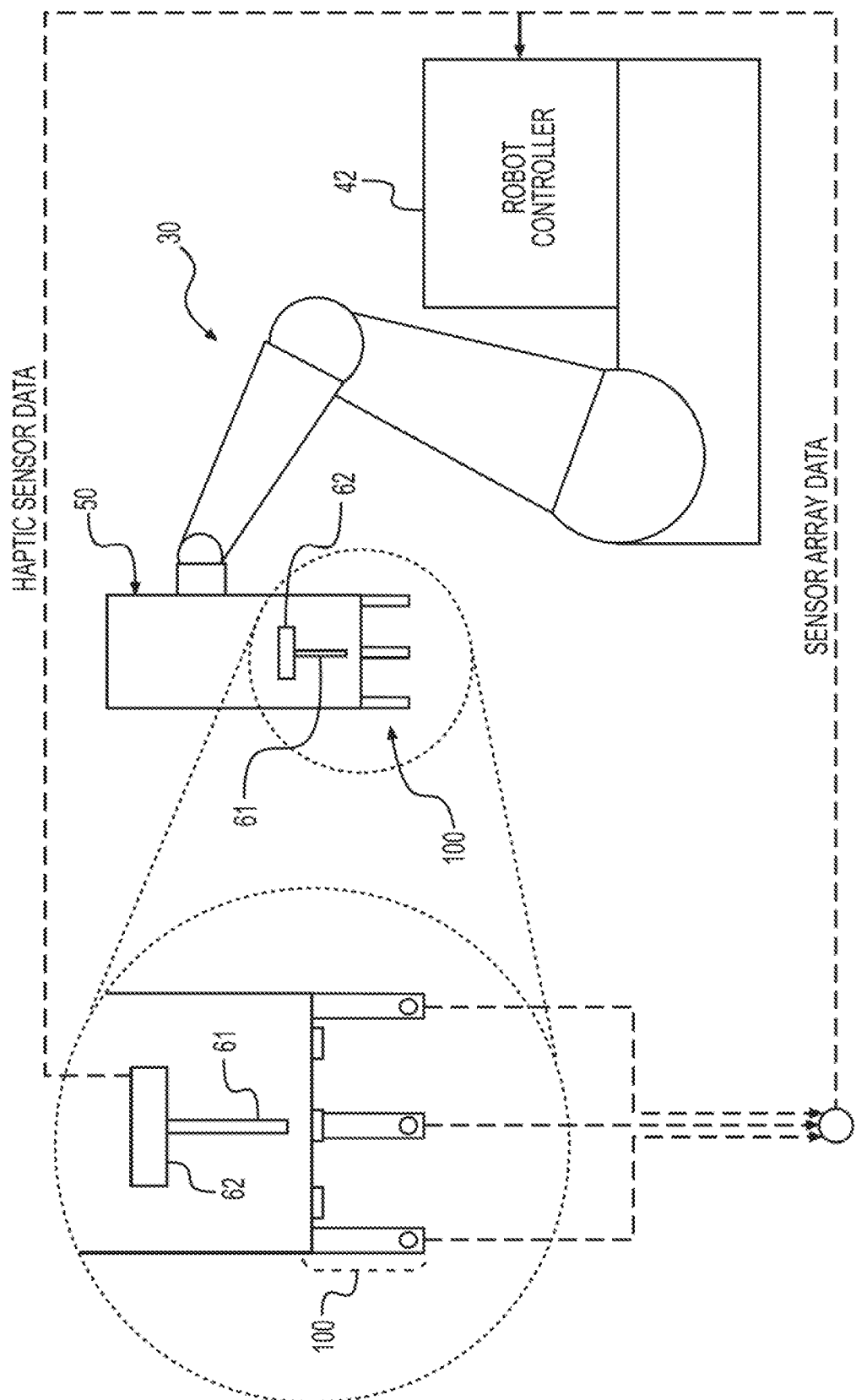
FIG. 8 is a schematic diagram of the IORT system shown in FIGS. 1A and 1B with a detailed view of the haptic control assembly and the sensor array.

To accelerate the electrons and with reference to FIG. 6, the treatment head 50 includes an elongate accelerator 51, a magnetron and RF control system 52 coupled to the accelerator 51, and an electron gun 53 coupled to one end of the accelerator 51. The magnetron and RF control system 52 utilizes high voltage pulses from a modulator and produces pulsed RF power that is delivered to the accelerator 51 through a circulator, the circulator being a component of the RF control in the magnetron and RF control system 52. The circulator typically allows RF power to flow from the magnetron to the accelerator 51 but prevents reflected RF power from reaching the magnetron by diverting it to a load.

The accelerator 51 is generally an elongate structure with a plurality of precisely machined cavities in vacuum so that each cavity has a very narrow resonance in the RF range. This resonance is matched at each cavity. To produce the desired electric fields, the magnetron and RF control system 52 generates RF power with a frequency that matches the resonant frequency of the accelerator 51. The control component of the magnetron and RF control system 52 includes an automatic frequency control (AFC) system that measures the reflected RF power returning from the accelerator 51 and adjusts the RF power frequency to minimize this reflected power to thereby match the resonant frequency of the accelerator 51. Collectively the magnetron, circulator, and AFC provide tuned RF power to the accelerator 51 setting up the electric fields necessary to accelerate an electron beam EB to therapeutically useful energies.

The electron gun 53 produces a population of free electrons within the vacuum of the accelerator 51. The electron gun 53 generally includes a heated cathode filament located near an electrically biased grid. An electron gun control 55 selectively activates the electron gun 53 and modulates the grid voltage to produce the beam of electrons during a beam pulse when RF power is also delivered to the accelerator 51. The electron beam EB traverses the length of the accelerator 51 increasing in energy along the way. Once the beam EB exits the accelerator 51, the electron beam EB passes through a beam monitor 54, typically an ionization chamber. A beam monitor interface 56 is coupled to the beam monitor 54, and both serve as a system for measuring and monitoring the absorbed dose delivered by the beam EB for a treatment in a treatment process. This dose information is provided to a main controller 200 (FIG. 16) and used to ensure the correct quantity of dose is delivered to the patient P.

The aligning of the treatment head 50 to a given applicator 80 is a relatively rapid two-stage process facilitated by components on the treatment head 50. The first stage is coarse positioning or alignment mainly performed by operation of haptic control assemblies 60 on the treatment head 50. The second stage is an automated fine alignment by the sensor array 100 coupled to the working end 50b of the treatment head 50.

Referring to FIGS. 1A, 1B, 3-5, and 7-9, one or more haptic control assemblies 60 are mounted on opposing sides of the treatment head 50. The placement of the haptic control assemblies 60 enables both right-hand and left-hand operation by the user as well as allowing for convenient user access depending on user position relative to the treatment head 50. An example of a haptic control system is disclosed by Fantini et al., U.S. Pat. No. 8,588,368, which is hereby incorporated by reference in its entirety.

Each haptic control assembly 60 includes an elongate haptic handle 61 mounted to a force-torque sensor 62. The haptic handle 61 desirably extends along a parallel axis to the length of the treatment head 50. Each haptic handle 61 is configured to move in various directions which includes tilting movement relative to a mounting point where an end of the handle 61 meets the force-torque sensor 62, rotational movement about the long axis of the handle 61, vertical movement along the long axis of the handle 61, and translative movement where the handle 61 can move across a parallel plane to the face of the working end 50b a predefined, albeit relatively short, distance. During normal use, operation of the handle 61 usually involves one or more of these movements, and the actual movements may be minimal yet detectable by the force-torque sensor 62.

The robot arm assembly 30 also includes a robot controller 42 in communication with the force-torque sensor 62. The force-torque sensor 62 obtains measurements of the magnitude and direction of force or force vector F and/or magnitude and direction of torque T applied to the haptic handle 61 by the user in 3-D space relative to the force-torque sensor 62. This encompasses the movement and direction of the force/torque being applied on the handle 61. The force-torque sensor 62 generates signals based upon this data and transmits those signals to the robot controller 42. The robot controller 42, in turn, responds to these signals by calculating and generating movement commands for moving one or more components of the robot arm assembly 30, such as the arm members 34, 36, 38; the joints 33, 35, 37, 39, 40; and the turntable 31, to facilitate the desired movement and positioning of the treatment head 50 as dictated by the user-applied force F and/or torque T on the haptic handle 61.

Any movement of the haptic handle 61 by the user produces a direct corollary movement of the treatment head 50, which enables the user to physically sense and assess the results of the amount of force F and/or torque T being applied to thereby adjust such control movements as needed. Thus, the feedback is received through motion of the treatment head 50 in response to the applied force/torque on the handle 61. The speed of movement of the various members can also be proportional to the amount of force/torque being applied.

In use, the user tilts the haptic handle 61 in a desired direction with a desired amount of force F, which normally results in combined movements of the arm members 34, 36, 38 as well as rotation of the turntable 31 to translate the treatment head 50 in the direction of the of the applied force F. Applying torque T on the haptic handle 61 results in combined movements of the arm members 34, 36, 38 as well as rotation of the turntable 31 to rotate the treatment head 50 about the axis of the applied torque T. For example, if the user desires to move the treatment head 50 from a start position, an arbitrary point A, where the working end 50b faces the ground to an end position, an arbitrary point B, where the treatment head 50 is elevated higher and a predetermined distance away from point A with the treatment head 50 pitched up at an angle, the user pushes and tilts the haptic handle 61 in the general direction of point B. This causes the treatment head 50 to translate in that general direction vis-à-vis the corresponding movements of the robot arm assembly 30. Simultaneous application of torque on the handle 61 will also cause the treatment head 50 to be rotated in the torque direction. Both of these manipulations of the handle 61 are continued until the desired orientation is assumed at point B.

Normally, the user operates only one of the haptic handles 61 at a time, since each haptic control assembly 60 is capable of facilitating the full range of movement of the robot arm assembly 30. To ensure this mode of operation, each haptic handle 61 can include a motion-enable switch or button 63 mounted thereon that must be selectively actuated for the robot controller 42 to respond to any movement of the haptic handle 61 by the user.

Figure 9:
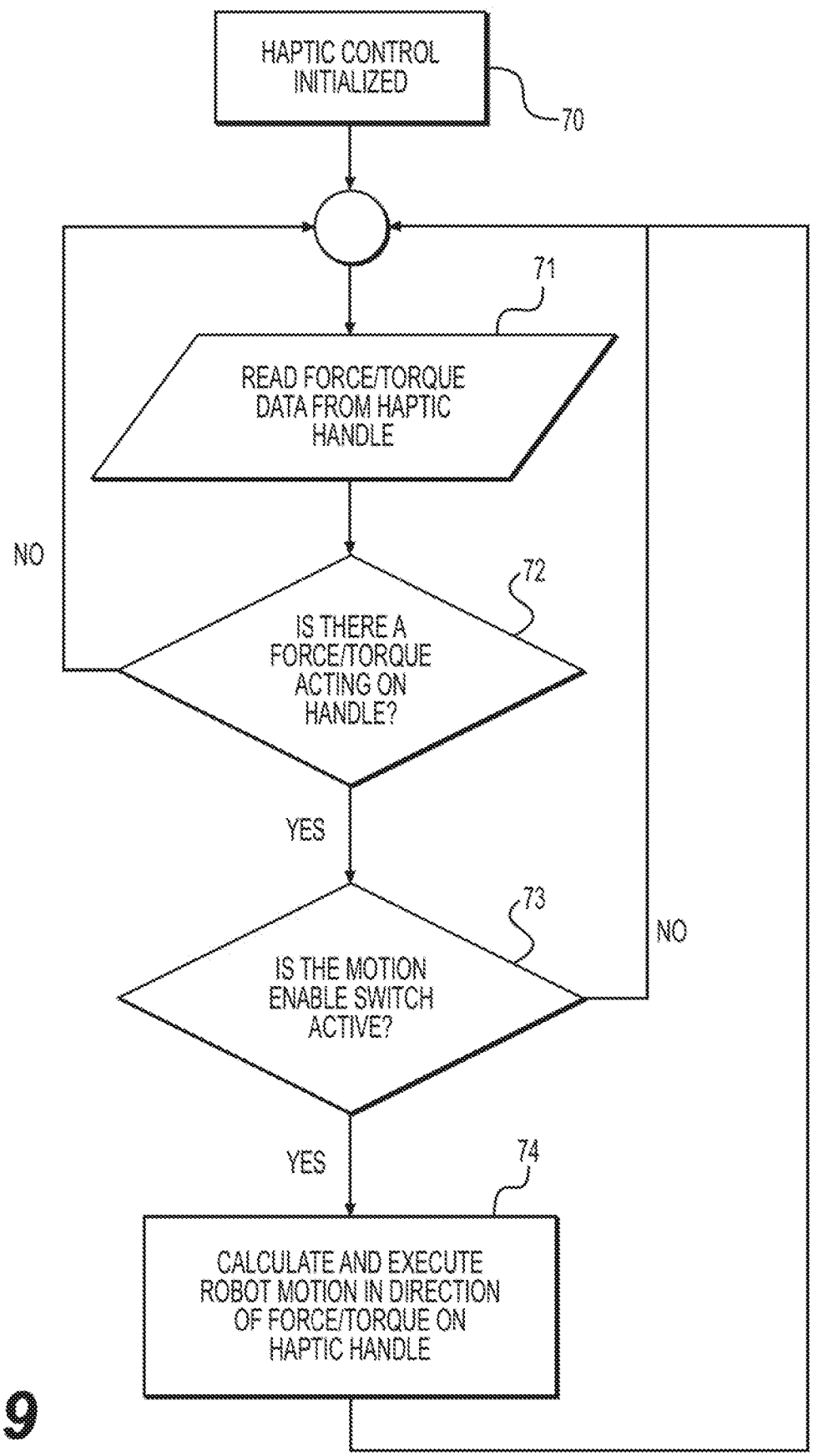
FIG. 9 is a flow chart of the haptic control assembly operation in the IORT system shown in FIGS. 1A and 1B.

Referring to FIG. 9, this flow diagram shows the operational steps followed by the haptic control assembly 60 as described above. Initially, the operation of the haptic control assembly 60 is initialized by selective activation of this function from the control panel 150 coupled to the cart 20 as at step 70. The details of the control panel 150 will be further discussed below. Initialization of the haptic control assembly 60 places the assembly 60 into a ready state for reading force/torque data from the haptic handle 61 as at step 71. If the user applies any force/torque (step 72), the system checks the active state of the motion-enable switch 63. If the motion-enable switch 63 is inactive, then the robot arm assembly 30 cannot be moved in response to movement of the haptic handle 61 and remains in the ready state. On the other hand, if the motion-enable switch 63 is active (step 73) via an active press of the button, then the system will calculate and execute the desired motion (step 74). The inclusion of the motion-enable switch 63 serves as an interlock that prevents any undesired movement of the robot arm assembly 30 during use. Other means of selective activation of the haptic control assembly 60 can also be used such as requiring exertion of a predetermined amount of force on the handle 61 to overcome a predetermined threshold in order to ensure movement of the robot arm assembly 30 is actually desired or intended. Another can include implementing a locking means on the handle 61 that must be unlocked prior to use.

Though the haptic control assemblies 60 are disclosed as a single handle operation, it is also contemplated that both handles 61, 61 can be used where a combination of applied force and/or torque from both enables movement of the robot arm assembly 30. For example, tilting of one handle 61 in one direction and simultaneous tilting of the other handle 61 in the opposite direction results in a clockwise or counter clockwise rotation of the turntable 31. Other examples include but are not limited thereto, pulling both handles 61, 61 towards the user to raise the treatment head 50, and conversely, pushing both handles 61, 61 away from the user lowers the treatment head 50. Each handle 61 can also function as a motion-enable switch for the other, e.g., operation of a select handle 61 requires a predetermined action on the other handle 61 prior to use. Moreover, the haptic control assemblies 60 can be positioned anywhere on the treatment head 50, even on the same side, at any orientation so long as the haptic handles 61 are easily accessible by the user. Furthermore, one or more of the haptic control assemblies 60 can be remotely placed from the treatment head 50, e.g., on the cart 20 or a remote console. However, placement on the treatment head 50 is generally more desired due to a more direct correlative and accurate positioning that can be performed by the user with close proximity and spatial awareness of the treatment head 50 and the applicator 80.

The second alignment stage involves the sensor array 100 that senses predetermined features of the applicator 80. In the field of IORT devices, the applicator 80 is generally an apparatus or device that collimates or narrows the emitted electron beam EB from the treatment head 50 to shape the beam into a form suitable for treatment. In a typical prior art soft-dock procedure, the applicator 80 is normally fixed in position relative to the treatment target area of the patient P by some means. The treatment head 50 is then manually brought into alignment, i.e., docked, with the applicator. In a hard-dock configuration, the applicator 80 is fixed to the treatment head 50, and no alignment between the applicator 80 and treatment head 50 is necessary since both are already aligned. The current IORT system 10 also performs a soft-docking operation except the final alignment is performed automatically.

As best shown in FIGS. 1A, 1B, 3, 4, 10A, 10B, and 11, the applicator 80 of the IORT system 10 includes an elongate cylindrical tube 82 and an open endcap 81 mounted to one end or proximal end of the tube 82. The endcap 81 is generally a hollow cylindrical disk-shaped member with a predetermined outer diameter and an axial length where the outer diameter defines an outer cylindrical surface 81g along this axial length. The top of the endcap, or proximal end in relation to operating orientation with respect to the treatment head 50, defines an annular, planar top surface 81f with a center bore or opening 81a formed thereon. The center bore 81a has a diameter 81h at least about the same as the diameter of a beam nozzle 57 on the working end 50b and communicates with a hollow interior extending substantially through the axial length of the endcap 81. This hollow interior defines an inner diameter 81j of the endcap 81.

Figure 10A:
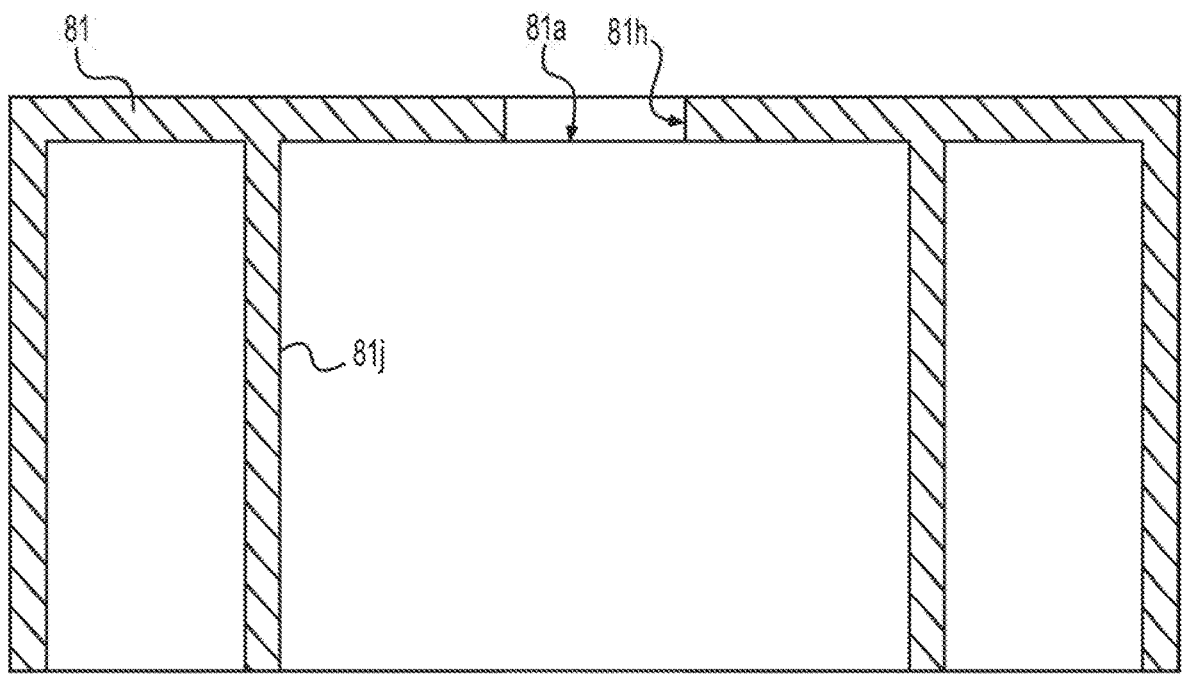
FIG. 10A is a sectional view of an endcap for an applicator in the IORT system shown in FIGS. 1A and 1B.

The tube 82 also has an outer diameter and an inner diameter defined by the hollow interior and the wall thereof. The outer diameter of the endcap 81 is desirably greater than the outer diameter of the tube 82 because the endcap 81 serves as a shield or buffer that prevents excess area of the beam EB from reaching the patient by travelling along the side of the tube 82. The center bore 81a and the hollow interior of the endcap 81 also serve as an initial means of collimating the electron beam EB through the tube 82 when assembled. The hollow interior of the tube 82 defines a guided passageway for traversal of the emitted electron beam EB from the treatment head 50 and simultaneously shapes the beam EB to direct the same towards the target area on the patient P. To ensure that the desired beam geometry is maintained throughout the applicator 80, the inner diameter 81j is at least the same as the outer diameter of the tube 82 with the center bore 81a, hollow interior of the endcap 81, and the hollow interior of the tube 82 being in direct communication with each other when assembled. Such a construction with relatively close tolerances enables the endcap 81 to detachably press fit onto the proximal end of the tube 82. This also enables the applicator 80 to be disassembled and reused following medical cleaning and sterilization practices. As best seen in FIG. 10A, the difference between the inner diameter 81h and the inner diameter 81j forms an annular ledge that serves as an abutment preventing the mounted end of the tube 82 from sliding out the top of the endcap 81. The outer diameter of the endcap 81 can range from about 10 cm to 15 cm, and the inner diameter 81j can range from about 3 cm to 10 cm. Correspondingly, the outer diameter of the tube 82 can range from about 3 cm to 10 cm. These dimensions should be construed in a non-limiting sense and can be varied depending on application and use.

Figure 10B:
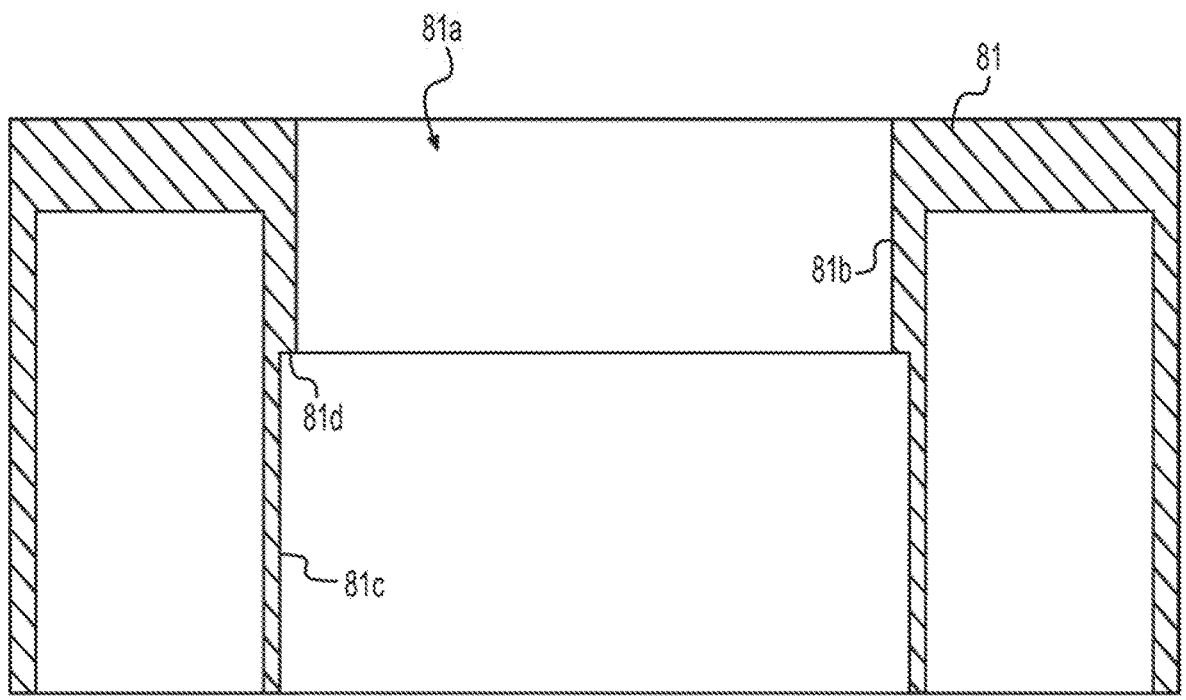
FIG. 10B is a sectional view of an alternative endcap for the applicator in the IORT system shown in FIGS. 1A and 1B.

Alternatively, the endcap 81 can be constructed with the center bore 81a having a stepped configuration as shown in FIG. 10B. This results in the center bore 81a being divided into an upper, first inner diameter 81b near the proximal end of the endcap 81 and a lower, second inner diameter 81c along a tube mounting portion near the distal end of the endcap 81. The first inner diameter 81b can be about the same or less than the inner diameter of the tube 82 while the second inner diameter 81c desirably matches the outer diameter of the tube 82. The difference between the first inner diameter 81b and the second inner diameter 81c forms an annular ledge or abutment 81d for the proximal end of the tube 82 to seat against when assembled. As such, the first inner diameter 81b is desirably less than the second inner diameter 81c. The thickness of the abutment 81d is desirably thick enough to securely support the abutted engagement with the tube 82. This type of construction will still be a press fit mounting of the endcap 81 onto the tube 82. However, the extent of mounted engagement between these parts is predetermined and maintained which prevents the endcap 81 from sliding along the tube 82 when assembled.

As noted above, the applicator 80 must be fixed in position relative to the patient P in a soft-docking process. To facilitate fixed positioning of the applicator 80, the IORT system 10 can include a clamp assembly 90 detachably mounted to an operating table or bed B. Most conventional operating beds B include one or more rails R on the sides to facilitate mounting of various instruments. The clamp assembly 90 is provided with three articulating arms, e.g., an elongate first arm 91, an elongate second arm 92, and an elongate third arm 93, pivotally coupled to each other. One end of the first arm 91 is slidably mounted to a select rail R and adjustably fixed thereon. One end of the second arm 92 and the third arm 93 are pivotal about a common lock joint 94 with respect to each other. The other end of the second arm 92 is provided with a ball joint 92a for pivotally coupling to the opposite end of the first arm 91. The other end of the third arm 93 also includes a ball joint 93a for pivotally coupling a clamp ring 95 thereon. The articulating arms 91, 92, 93 and the joints 92a, 94, 93a comprise a type of holding system manufactured and sold by Fisso Swiss Made, a subsidiary of Baitella A G with its place of business in Thurgauerstrasse 70, CH-8050, Zurich. In such a holding system, once the arms 91, 92, 93 have been manipulated to a desired position, the lock joint 94 can be actuated to lock all the joints 92a, 94, 93a thereby fixing the relative position of all the arms 91, 92, 93. The clamp ring 95 provides a suitable opening for slidable mounting of the tube 82 therein. When the desired position of the applicator 80 has been placed within the clamp ring 95, a clamp setscrew 96 fixes the position of the tube 82.

Referring to FIG. 11, the IORT system 10 can be provided with a variety of applicators for treating target areas of various dimensions. For example, FIG. 11 shows three sets of applicators ranging from a small applicator 80a, medium applicator 80b, and a large applicator 80c. The descriptors "small," "medium," and "large" refer to the relative diameters of the applicator tube in each set. The outer diameter of the respective endcaps is the same.

The small applicator 80a includes an endcap 83 with a center bore 83a configured for detachable mounting to the proximal end of a straight tube 84a or a beveled tube 84b. The inner diameter of the center bore 83a matches the outer diameter of both tubes 84a, 84b. Though not clearly shown in previous Figures, the endcap 83 can be a generally hollow member with a plurality of radial ribs 83e extending from the center bore 83a to the outer wall of the endcap 83 to strengthen and reinforce the structure of the endcap 83. Moreover, this construction reduces the weight of the endcap as compared to a solid or substantially solid disk. The straight tube 84a is provided with a straight, perpendicular output or distal end while the beveled tube 84b is provided with a beveled output or distal end. Most normal applications of the IORT system 10 utilizes applicators 80 with a straight tube such as the straight tube 84a. There are instances, however, where a beveled output end, such as one provided by the beveled tube 84b, would be more suitable by conforming better with the contours of the target site on the patient P. Due to the variance in physiology from patient to patient, the angle of the bevel can be varied for a specific patient.

The medium applicator 80b and the large applicator 80c are similarly constructed as the small applicator 80a. As such, the medium applicator 80b includes an endcap 85 with a center bore 85a and radial ribs 85e configured for selective coupling to a straight tube 86a or a beveled tube 86b. The diameters of the straight tube 86a and the beveled tube 86b are the same but greater than the diameters of the straight tube 84a and the beveled tube 84b. The large applicator 80c includes an endcap 87 with a center bore 87a and radial ribs 87e configured for selective coupling to a straight tube 88a or a beveled tube 88b. The diameters of the straight tube 88a and the beveled tube 88b are the same but greater than the diameters of the straight tube 86a and the beveled tube 86b. It is noted that the examples described above are to be construed in a non-limiting sense and can be varied depending on application and use. Moreover, the tube component of the applicator 80, 80a, 80b, 80c can be constructed in a variety of cross sectional, geometric shapes, such as square, triangle, hexagonal, and the like. Furthermore, the clamp assembly 90 described above can be used in all variants of the applicator 80.

The following description of the sensor array 100 makes reference to the applicator 80 for brevity and clarity. The functions of the sensor array 100 apply equally to the applicator variants shown in FIG. 11. As mentioned above, the sensor array 100 senses predetermined features of the applicator 80, more specifically, the top annular, planar surface 81f of the endcap 81 and the cylindrical outer surface 81g of the endcap 81. Additionally, the IORT system 10 is already provided with dimension data of the endcap 81, such as the outer diameter, which serves as a baseline for comparing sensed data and enable subsequent adjustments. The sensor array 100 includes a plurality of proximity sensors divided into a first sensor set 110 for detecting the top surface 81f and a second sensor set 120 for detecting the outer surface 81g. These sensors are desirably optical sensors using laser light to detect an object surface and measure relative distance thereof from the sensor. In an embodiment, the sensors employed in the sensor array 100 are rated to operate within a range of about 25-100 mm. It is to be understood, however, that any proximity sensor such as a capacitive displacement sensor, inductive sensor, magnetic sensor, ultrasound sensor, radar, and the like with varying operational ranges can be employed as long as they have similar or better detection and measurement performance as the optical laser sensor.

Figure 5:
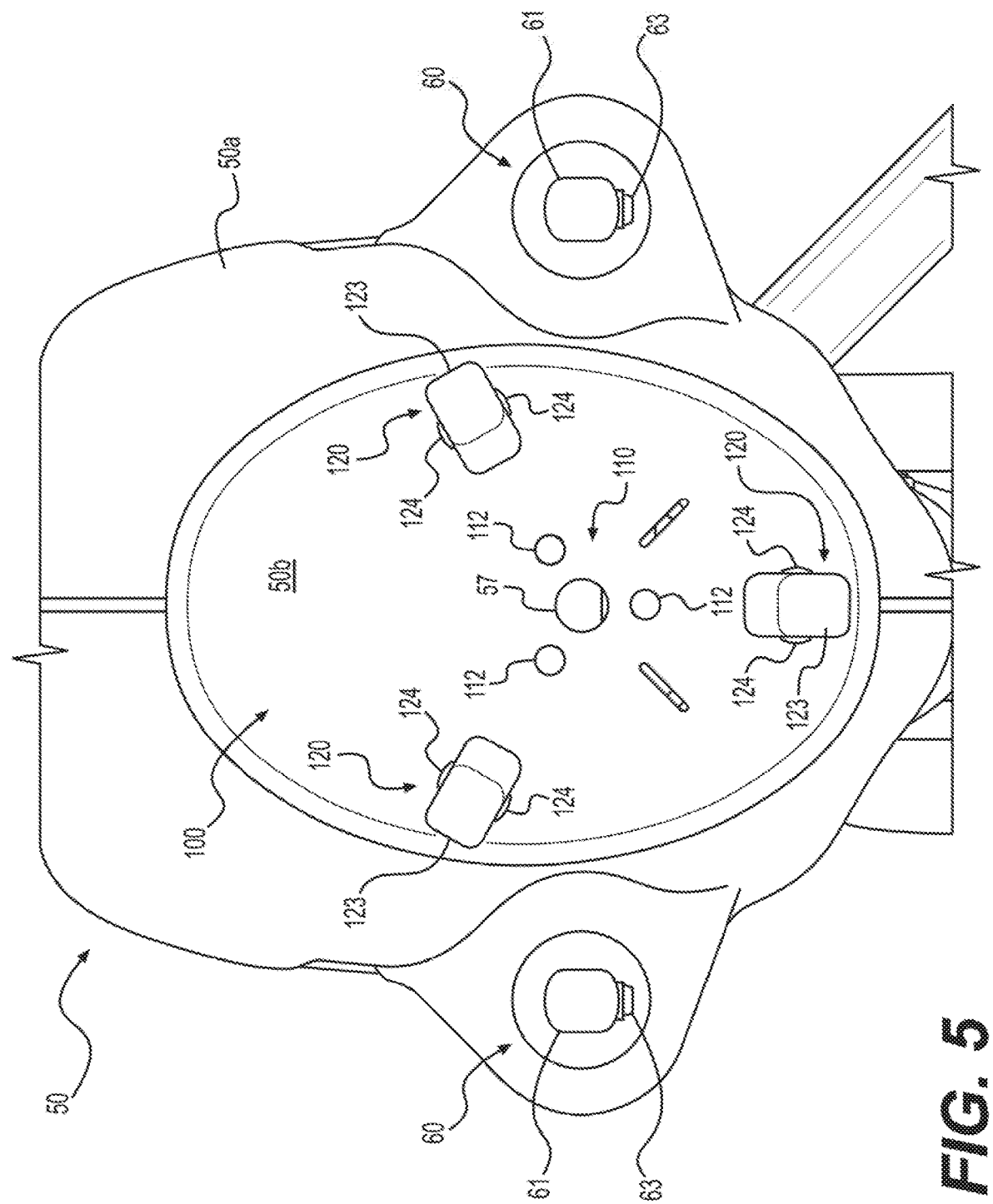
FIG. 5 is a bottom, detailed perspective view of a working end and sensor array on the treatment head of the IORT system shown in FIGS. 1A and 1B.

Referring to FIGS. 1A, 1B, 3-5, 12A, and 12B, the first sensor set 110 comprises a plurality of axial alignment sensors 112 arranged on the working end 50b of the treatment head 50 in an equidistant, circular pattern centered around an axis of a beam aperture or nozzle 57 where the electron beam EB exits from the treatment head 50. The working end 50b can be a faceplate upon which components of the sensor array 100 can be attached and enable the beam nozzle 57 to axially extend from the treatment head 50. The first sensor set 110 thus forms an inner ring of sensors. In an embodiment, three of these axial alignment sensors 112 are desired so each defines a point of an equilateral triangle as shown in FIG. 5. The axial alignment sensors 112 are mounted on the working end 50b to direct laser light downstream of and along parallel axes to the beam nozzle 57. This arrangement enables the axial alignment sensors 112 to detect object surfaces and determine the relative distance of the object surfaces that intersect along the electron beam EB path within the operational limits of the sensors. Since the axial alignment sensors 112 are configured to detect and measure the top surface 81f, these sensors 112 are arranged so the detection area lies within the outer diameter of the endcap 81.

Figure 12B:
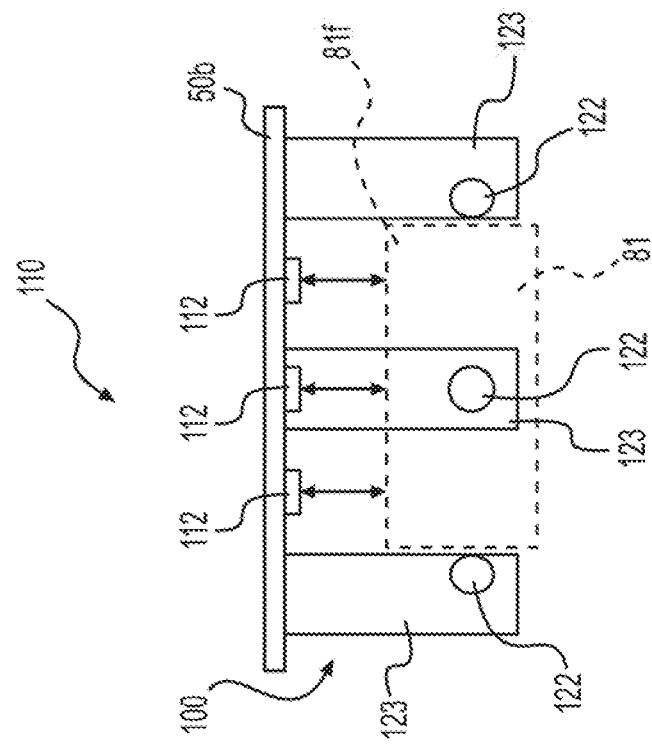
FIG. 12B is a schematic diagram of the first sensor set on the sensor array shown in FIG. 12A, the first sensor set being in an aligned position relative to the top surface of the endcap after adjusting position from FIG. 12A.
Figure 12A:
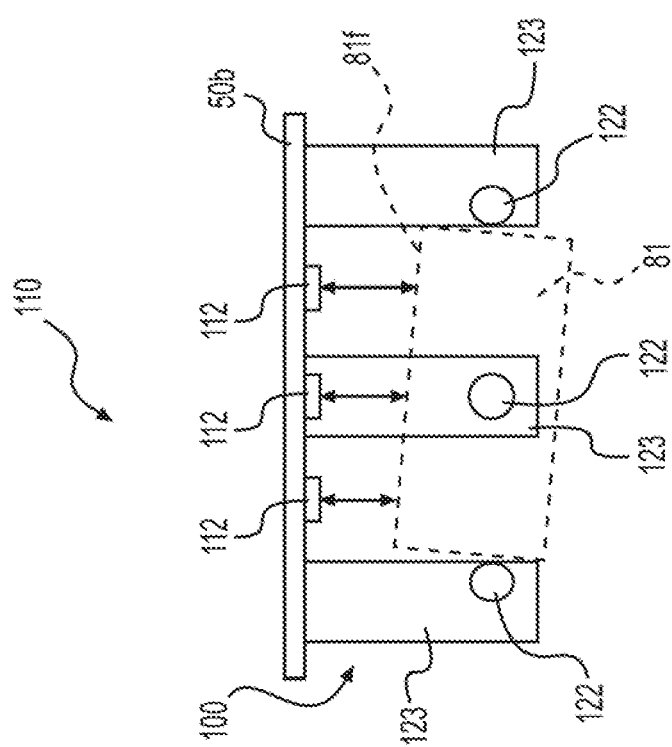
FIG. 12A is a schematic diagram of a first sensor set on the sensor array in the IORT system shown in FIGS. 1A and 1B, the first sensor set detecting a misaligned position of a top surface of an endcap after coarse alignment.

As best seen in FIGS. 12A and 12B, FIG. 12A shows the relative positions of the axial alignment sensors 112 and the top surface 81f of the endcap 81 when the coarse alignment has been made in the manner previously described. It can be seen that the top surface 81f is skewed relative to a vertical axis such that each axial alignment sensor 112 is reading a different relative axial distance of the respective detection point on the top surface 81f from the other thereby indicating mismatched proximity readings from the generated relative proximity data from the axial alignment sensors 112. These distances are represented by double ended arrows in the Figures. For proper alignment, the flat top surface 81f must be the same distance at each sensor 112. To correct the axial misalignment shown in FIG. 12A, the positions of the treatment head 50 and/or the robot arm assembly 30 are automatically adjusted based upon the sensed distance readings from the axial alignment sensors 112 until the correct aligned position of the treatment head 50 has been reached as shown in FIG. 12B. This corrected alignment places the axis of the applicator 80 parallel to the exiting beam axis.

As noted above, at least three of the axial alignment sensors 112 are desired to obtain a proper reading of the surface relative to the sensors. The top surface 81f of the endcap 81 is flat, and the area of this surface exists within a two coordinate axes plane. If only one or two sensors are employed, the former would only measure a select point or line on the surface without consideration of the tilt or elevational layout of the surrounding area, and the latter would only measure the relative distance along a line or single coordinate axis. Thus, the three axial alignment sensors 112 generate relative proximity data and are desired since they provide three data points encompassing the surface area being sensed rather than a point or line. It is noted that more than three of the axial alignment sensors 112 may be employed for similar effect. Alternatively, any number of sensors that can measure multiple relative distances of a substantial part or whole of a given surface area can also be employed.

The first sensor set 110 facilitates axial alignment of the applicator 80. Radial alignment must also be performed to place the axis of the applicator 80 coincident with the axis of the beam nozzle 57. Referring to FIGS. 1A, 2B, 3-5, 13A, and 13B, the second sensor set 120 comprises a plurality of radial alignment sensors 122 arranged on the working end

50b on the treatment head 50 in an equidistant, circular pattern centered around the axis of the beam nozzle 57. The radial alignment sensors 122 are radially spaced further apart than the axial alignment sensors 112 so as to loosely accommodate the given outer diameter of the endcap 81. Due to the wider radial spacing, the second sensor set 120 forms an outer ring of sensors. In an embodiment, three of these radial alignment sensors 122 are desired so each defines a point of an equilateral triangle similar to the axial alignment sensors 112 as shown in FIG. 5. Each radial alignment sensor 122 is mounted to a distal end of a corresponding radial sensor support 123 extending downwardly in spaced relation from the working end 50b. These radial sensor supports 123 can be straight, angled, curved, or combination thereof elongate members that can sturdily support the respective radial alignment sensor 122 in spaced relation from the axial alignment sensors 112. The radial alignment sensors 122 are mounted on the working end 50b to direct laser light downstream of and orthogonal to the electron beam axis. This arrangement enables the radial alignment sensors 122 to detect object surfaces, generate relative proximity data and determine the relative distance of the object surfaces along paths orthogonally intersecting the electron beam EB axis within the operational limits of the sensors.

As best seen in FIGS. 13A and 13B, FIG. 13A shows the relative positions of the radial alignment sensors 122 and the outer surface 81g of the endcap 81 when the coarse alignment has been made in the manner previously described. It can be seen that the outer surface 81g is radially offset relative to the axis of the beam nozzle 57 such that each radial alignment sensor 122 is reading a different relative radial distance of the respective detection point on the outer surface 81g from the other thereby indicating mismatched proximity readings from the generated relative proximity data from the radial alignment sensors 122. These distances are represented by double ended arrows in the Figures. For proper alignment, the distance of the outer surface 81g from each sensor 122 must be the same. Since the outer diameter of the endcap 81 is given and the relative positions of the radial alignment sensors 122 are equal and fixed, the IORT system 10 can calculate the exact relative distance of the outer surface 81g that must be reached for proper alignment. To correct the radial misalignment shown in FIG. 13A, the positions of the treatment head 50 and/or the robot arm assembly 30 are automatically adjusted based upon the sensed distance readings from the radial alignment sensors 122 until the correct aligned position of the treatment head 50 has been reached as shown in FIG. 13B. This corrected alignment places the axis of the applicator 80 coincident with the exiting beam axis assuming the axial alignment has been performed. It is noted that the corrective adjustments can be performed sequentially in any order or at the same time.

As noted above, at least three of the radial alignment sensors 122 are desired to obtain a proper reading of the surface relative to the sensors. The triangular arrangement of the radial alignment sensors 122 enables the IORT system 10 to triangulate the relative position of the endcap 81 so as to accurately and easily center the treatment head 50 relative to the applicator 80. More than three of such sensors can be employed for similar effect since they can generate more data points for comparison, especially for cylindrical objects. Less than three sensors can be employed if they can provide similar relative distance data. For example, an orbiting scanner attached to and centered on the working end 50b can provide similar functionality. A pair of diametrically opposed sensors provides two points of data which may be sufficient for some use scenarios but not as consistently accurate as with three sensors in the manner described above.

Figure 14:
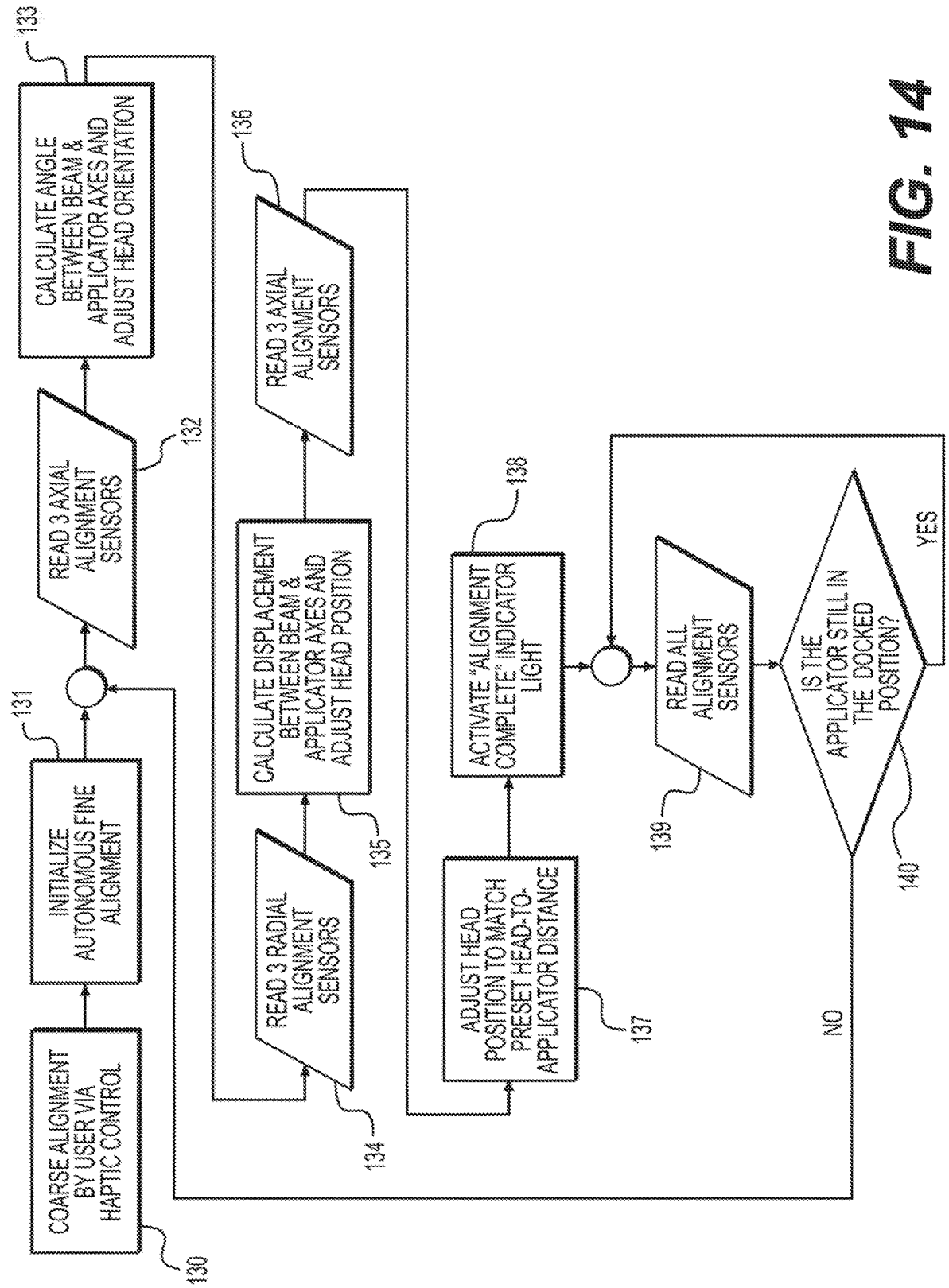
FIG. 14 is a flow chart of an alignment process performed by the IORT system shown in FIGS. 1A and 1B.

Referring to FIG. 14, this flow diagram shows the operational steps followed by the IORT system 10 as described above in relation to the two-stage alignment process. The alignment process begins with the above described coarse alignment facilitated by the haptic control assemblies 60 (step 130) where the sensor array 100 is brought into sensing range of the endcap 81. Each of the radial sensor supports 123 can be provided with one or more indicator lights 124 that flash in a predetermined sequence or pattern to indicate establishment of the coarse alignment. Other types of light effects such as specific color, luminosity, intensity, and the like can be used alone or in combination with the sequence or pattern.

The IORT system 10 is then initialized via the control panel 150 to commence autonomous fine alignment (step 131). Within steps 132 and 133, the IORT system 10 takes readings from the axial alignment sensors 112 (step 132) and calculates the angle between the beam axis and the applicator axis. The orientation of the treatment head 50 is adjusted according to this calculation of the angle (step 133). Similarly, the IORT system 10 takes readings from the radial alignment sensors 122 and calculates the displacement between the beam axis and the applicator axis (steps 134 and 135). The orientation of the treatment head 50 is further adjusted according to this calculation of the displacement (step 135). Readings from the axial alignment sensors 112 are repeated (step 136) to determine whether the relative distance of the top surface 81f matches a predetermined head-to-applicator distance. If not, then the treatment head 50 position is adjusted to match this predetermined distance (step 137). The head-to-applicator distance is desirably controlled in a precise manner from a clinical physics perspective. This distance has been calculated to ensure consistency of the radiation dose delivered to the patient P. The indicator light 124 can be activated again in a different pattern or a continuous "ON" state for a predetermined period to indicate completion of the fine alignment (step 138).

After completion of the fine alignment, the treatment head 50 can be activated to deliver the desired dose of radiation, the treatment activation normally being facilitated from a nearby shielded area. During the actual treatment phase, the IORT system 10 monitors the relative position of the treatment head 50 and the applicator 80 by taking constant readings from the axial alignment sensors 112 and the radial alignment sensors 122 (step 139). If proper alignment is maintained, i.e., the applicator 80 is still in the proper docked position, then the IORT system 10 continues to monitor the relative position. If for some reason misalignment occurs, the IORT system 10 reverts to making fine alignment adjustments (step 140) as necessary. For example, if misalignment occurs during treatment, the treatment is ceased so as to prompt the user to investigate the cause of misalignment and confirm the treatment setup. If misalignment occurs during treatment setup, then the user is prompted to repeat the autonomous alignment process.

Figure 15:
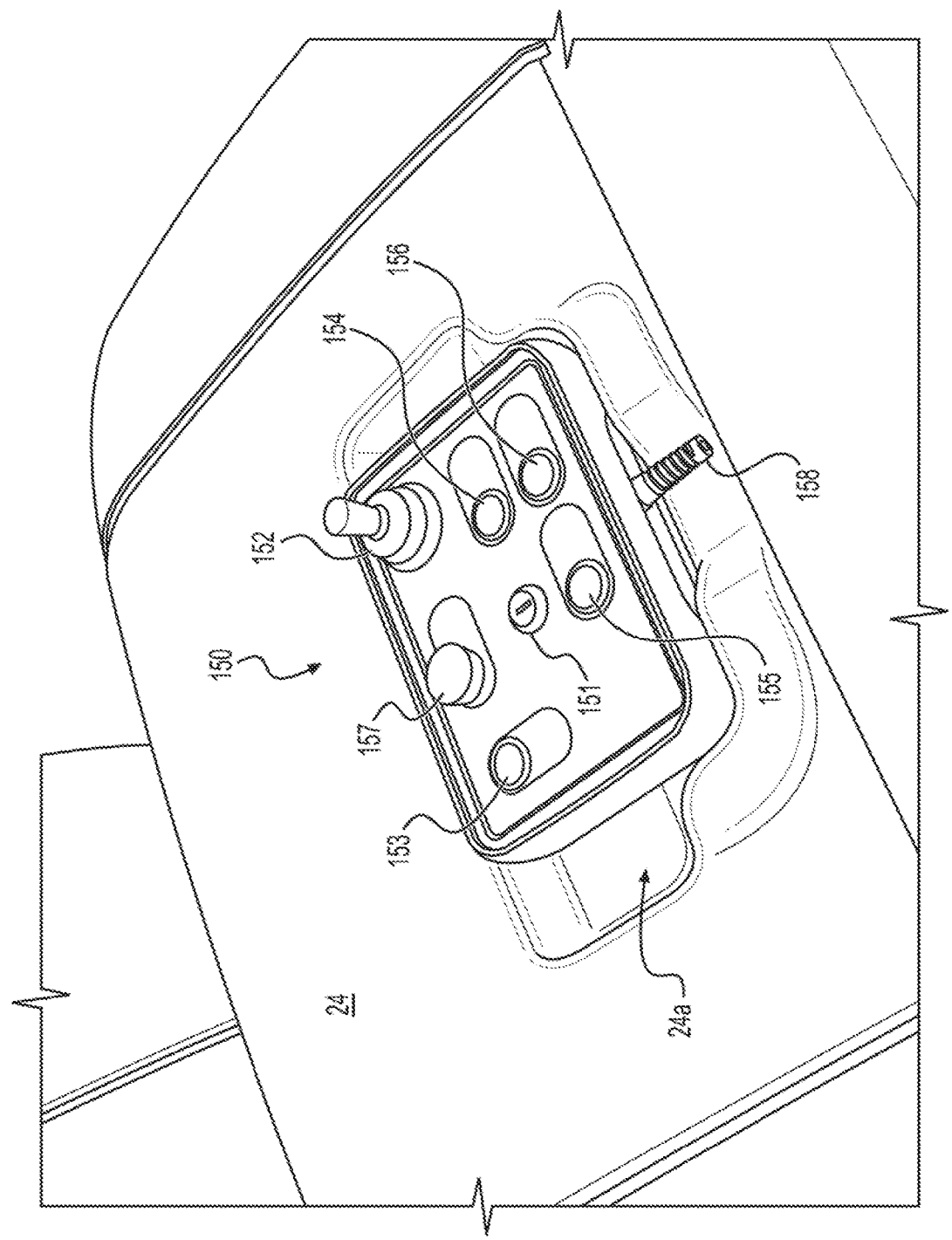
FIG. 15 is a detailed perspective view of a control panel for the IORT system shown in FIGS. 1A and 1B.

The operations of the IORT system 10 such as movement of the cart 20 and the alignment of the treatment head 50 are facilitated by the control panel 150. The control panel 150 serves as a user interface that communicates with the main controller 200 (FIG. 16), and the main controller 200 controls the various functions based on input from the control panel 150. As best shown in FIG. 15, the control panel 150 is generally a thin box with a plurality of activator switches mounted to a top face thereof. The control panel 150 is desirably portable to enable the user to control the various functions from a remote location relative to the cart 20 and the robot arm assembly 30. When not in use or when remote operation is not necessary, the control panel 150 can be stowed onto a control panel recess 24a formed on the rear shelf 24. A connector 158 extends from a side of the control panel 150 for selective, operating connection to the main controller 200. The connector 158 permits a hard connection to the main controller 200. However, it is also contemplated that the control panel 150 can also communicate with the main controller 200 wirelessly, such as with Bluetooth® technology and the like.

A key switch 151 on the control panel 150 toggles the IORT system 10 between three different modes, an "OFF" mode, a cart mode, and a head/robot mode. Toggling between cart mode and head/robot mode ensures that operation of the cart 20 and operation of the robot assembly 30 are independent. This provides a measure of safety so that there is no unintentional movement of the robot assembly 30 during cart movement and vice versa. In cart mode, the cart mode enables the user to drive the cart 20 to the desired location, and the control panel 150 includes a joystick 152 to facilitate steering and/or driving the cart 20 while the key switch 151 is toggled to the cart mode. As a further safety measure, the control panel 150 includes a motion-enable switch or button 153 that must be continuously activated during any movement of the cart 20 or the robot arm assembly 30. This motion-enable switch 153 is separate from the motion-enable switch 63 in the haptic control assembly 60, and operation of the motion-enable switch 63 is not dependent on activation of the motion-enable switch 153 and vice versa.

In head/robot mode, the head/robot mode enables several different functions of the robot arm assembly 30 and the attached treatment head 50. The control panel 150 is provided with three different switches or buttons dedicated to these functions, a ready switch 154, a park switch 155, and an align switch 156.

Selective activation of the ready switch 154 and concurrent activation of the motion-enable switch 153 while the key switch 151 is toggled to the head/robot mode moves the robot arm assembly 30 autonomously into a ready position or ready state, this position or state being one in which the robot arm assembly 30 is unfolded and the treatment head 50 is elevated to a suitable height where the haptic control assembly 60 can be accessed and ready for coarse alignment by the user, such as the approach position of the IORT system 10 shown in FIG. 1A. The user continuously activates the motion-enable switch 153 during this process until the ready position or ready state has been assumed. In the ready position, the robot arm assembly 30 is not fully extended but rather unfolded enough to have the treatment head 50 raised above the bed B so as to ensure that there will be plenty of room for alignment movements and no inadvertent impacts with the bed B, patient P, or the applicator 80. Moreover, this ready position permits movement of cart 20 towards the bed B without undue concern for imbalance or potential accidents, since transport of the IORT system 10 in the ready position is usually undertaken for short trips, such as when moving the IORT system 10 from a corner of the OR to the patient P. Additionally, after treatment completion, the user activates the ready switch 154 and the motion-enable switch 153 to autonomously retract the treatment head 50 back to the ready position from a treatment position, an example of which is shown FIG. 1B. The treatment head 50 assumes the ready position or ready state by retracting a predetermined distance along the alignment axis relative to the applicator 80 and pitches up or down as the arm members 34, 36, 38 fold depending on the assumed position of the treatment head 50 during treatment. This retraction of the treatment head 50 along the alignment axis is desired because it is an established safe path to move the treatment head 50.

Selective activation of the park switch 155 and concurrent activation of the motion-enable switch 153 while the key switch 151 is toggled to the head/robot mode moves the robot arm assembly 30 autonomously into a parked position or parked state where the arm members 34, 36, 38 fold into a compact form. The user continuously activates the motion-enable switch 153 during this process until the park position or park state has been assumed. In the park position or park state, the treatment head 50 can be positioned so that the working end 50b faces and vertically aligns with the ground or tilted at an angle back towards the tall section 22 of the cart 20. The former position of the treatment head 50 is generally more desired so as to minimize stresses on any cables attached thereto. For safety concerns, the park position is required prior to relative long-distance transport of the IORT system 10 vis-à-vis the cart 20.

The fine alignment with the assistance of the sensor array 100 as described above commences by selective activation of the align switch 156 and concurrent activation of the motion-enable switch 153 while the key switch 151 is toggled to the head/robot mode. At this point, the coarse alignment has placed the sensor array 100 within active range of the sensors 112, 122. Continuous activation of the motion-enable switch 153 enables movement of the robot arm assembly 30 and the treatment head 50 to autonomously align the treatment head 50 with respect to the applicator 80.

It can be seen from the above that the control panel 150 enables all motion-related functions of the cart 20, the robot arm assembly 30, and the treatment head 50 excluding coarse alignment which employs the haptic handles 61. In case of emergencies, the control panel 150 also includes a stop switch or button 157 that ceases all functions of the to IORT system 10. Another or secondary emergency stop switch is provided by a switch 159 on the cart 20 which may be closer for immediate activation should the stop switch 157 not be readily accessible.

Figure 16:
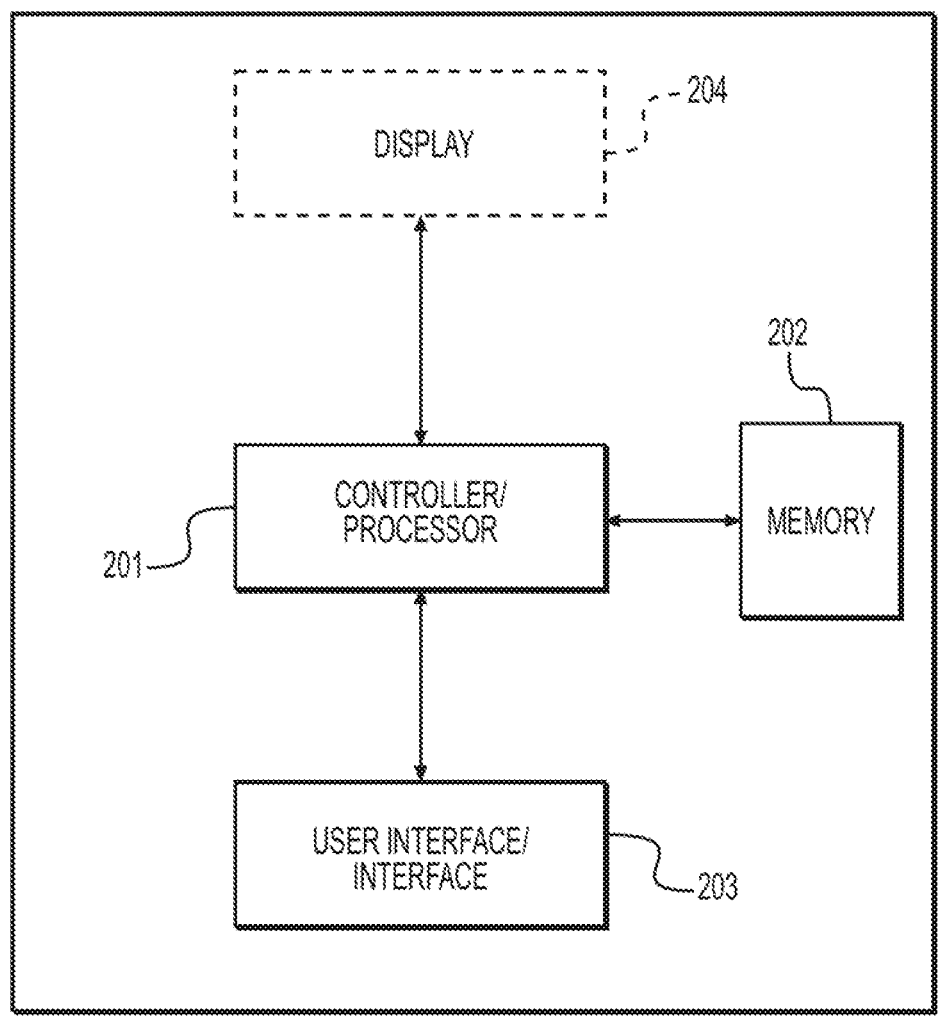
FIG. 16 is a block diagram of a main controller for the IORT system shown in FIGS. 1A and 1B.

Referring to FIG. 16, the main controller 200 controls operations of the IORT system 10 with input from the control panel 150. It should be understood that the main controller 200 may represent, for example, a stand-alone computer, computer terminal, portable computing device, networked computer or computer terminal, or networked portable device. In an embodiment, the main controller 200 is housed in the cart 20. Data may be entered into the main controller 200 by the user via any suitable type of user interface 203, such as the control panel 150, and may be stored in a computer readable memory 202, which may be any suitable type of computer readable and programmable memory. Calculations are performed by a controller/processor 201, which may be any suitable type of computer processor, and may be displayed to the user on a display 204, which may be any suitable type of computer display, such as a liquid crystal display (LCD) or a light emitting diode (LED) display, for example. Though not shown, such a display 204 can be connected to the IORT system 10 to provide desired information such as graphical representations of the alignment process, diagnostics, and the like.

The controller/processor 201 may be associated with, or incorporated into, any suitable type of computing device, for example, a personal computer or a programmable logic controller (PLC) or an application specific integrated circuit (ASIC). The display 204, the controller/processor 201, the memory 202, and any associated computer readable media are in communication with one another by any suitable type of data bus, as is well known in the art. In this manner, the main controller 200 is in communication with the robot controller 42.

Examples of computer readable media include a magnetic recording apparatus, non-transitory computer readable storage memory, an optical disk, a magneto-optical disk, and/or a semiconductor memory (for example, RAM, ROM, etc.). Examples of magnetic recording apparatus that may be used in addition to memory 202, or in place of memory 202, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

It can be seen from the above description that the alignment process can be a relatively quick and easy process. For coarse alignment, the user simply operates the haptic handle 61 until the endcap 81 is within operational range of the sensors 112, 122. Once the coarse alignment at a coarse alignment position is established, autonomous fine alignment commences upon initialization of the fine alignment process from the control panel 150. The alignment process has also been configured with careful appreciation for preserving the sterile environment in the OR. For example, the placement of the sensors 112, 122 ensures plenty of space for preventing contact with the endcap 81. Such a contact can potentially cause contamination and infection of the patient P due to the robot arm assembly 30, the treatment head 50, and/or the cart 20 not being suitably sterilized. Moreover, the various motion-enable switches 63, 153 ensure safe operation and positioning by forcing a check on the user with respect to the desired movement.

It is to be understood that the present invention is not limited to the embodiments described above, but encompasses any and all embodiments within the scope of the following claims.

We claim:

1. An intraoperative radiation therapy (IORT) system, comprising:
    a moveable cart adapted for selective transport;
    a robot assembly coupled to the cart, the robot assembly comprising:
        at least one elongate arm and at least five movement axes to increase positional flexibility and reach;
        a rotary turntable mounted to the cart, the turntable being selectively rotatable about a vertical first axis to facilitate selective rotational positioning of the robot assembly, the turntable having a base; and
        a radial section extending from the turntable, the radial section having a first pivot joint at a distal end offset from the base of the turntable, the first pivot joint defining a horizontal second axis orthogonal to the first axis, the at least one elongate arm being pivotally coupled to the first pivot joint;
    at least one applicator adapted to be fixed near a target area of a patient, the at least one applicator having an elongate tube and an open endcap detachably mounted to one end of the tube, the at least one applicator defining an applicator axis;
    a treatment head coupled to the at least one arm, the treatment head having a working end adapted to emit therapeutic beams towards the target area for radiation therapy, the treatment head adapted to be aligned with the applicator axis in a soft-docking process;
    at least one haptic control assembly coupled to the treatment head, the haptic control assembly configured to move the treatment head for a coarse alignment within detection range of the endcap on the applicator;
    a sensor array coupled to the working end of the treatment head, the sensor array having a plurality of sensors with a given operational range, the sensors adapted to detect surfaces on the endcap and measure relative distance therebetween, selective operation of the at least one haptic control assembly moving the sensor array within sensing range of the endcap for the coarse alignment; and
    a control panel associated with a controller having a plurality of switches for controlling movements of the cart, the robot assembly, and the treatment head,
    wherein after coarse alignment, selective operation of the control panel facilitates autonomous fine alignment of the treatment head based on sensed data from the sensor array.

2. The intraoperative radiation therapy system of claim 1, wherein the moveable cart comprises:
    a substantially L-shaped vehicle, when seen from a side, the substantially L-shaped vehicle having a bottom, a short front section, and a tall rear section congruent with the short front section, the short front section defining a front shelf configured to rotatably support the robot assembly, and the tall rear section defining a rear shelf to selectively support the control panel thereon; and
    a plurality of wheels mounted near the bottom of the substantially L-shaped vehicle to facilitate selective transport of the substantially L-shaped vehicle to a desired location.

3. The intraoperative radiation therapy system of claim 1, wherein the at least one elongate arm comprises:
    an elongate first arm member having one end pivotally coupled to the first pivot joint of the radial section to thereby selectively rotate about the second axis;
    a second pivot joint disposed on the opposite end of the first arm member, the second pivot joint defining a third axis spaced and parallel to the second axis;
    an elongate second arm member having one end pivotally coupled to the second pivot joint to thereby selectively rotate about the third axis, the coupling between the first arm member and the second arm member facilitating selective raising and lowering of the robot assembly within a vertical plane and thereby raise or lower the treatment head coupled to the at least one elongate arm;
    a third pivot joint disposed on the opposite end of the second arm member, the third pivot joint defining a fourth axis orthogonal to the second and third axes and coaxial with the second arm member;
    an elongate third arm member having one end pivotally coupled to the third pivot joint, the third arm member being coaxial with the second arm member, the third pivot joint facilitating selective rotation of the third arm member about the fourth axis; and
    a combination joint assembly disposed at the opposite end of the third arm member, the treatment head being coupled to the combination joint assembly to facilitate positioning of the treatment head with respect to the second arm member, selective rotation of the third arm member facilitating selective rotation of the treatment head about the fourth axis relative to the second arm member.

4. The intraoperative radiation therapy system of claim 3, wherein the combination joint assembly comprises:
a fourth pivot joint disposed on the opposite end of the third arm member, the fourth pivot joint defining a fifth axis orthogonal to the fourth axis, the fourth pivot joint facilitating selective forward and backward pitching of the treatment head about the fifth axis relative to the third arm member; and
a fifth pivot joint operatively coupled to the fourth pivot joint, the fifth pivot joint defining a sixth axis orthogonal to the fifth axis, the fifth pivot joint facilitating selective rotation of the treatment head about the sixth axis.

5. The intraoperative radiation therapy system of claim 1, wherein:
the at least one applicator comprises a plurality of applicators, each applicator having an endcap with the same predetermined outer diameter and length.

6. The intraoperative radiation therapy system of claim 5, wherein:
the plurality of applicators comprises at least one elongate tube having a diameter different from other elongate tubes of the plurality of applicators, an opposite end of each elongate tube being straight or beveled.

7. The intraoperative radiation therapy system of claim 1, wherein the treatment head comprises:
an elongate accelerator having an exit;
a magnetron and RF control system coupled to the accelerator, the magnetron and RF control system providing tuned RF power to the accelerator;
an electron gun coupled to one end of the accelerator, the electron gun configured to produce an electron beam;
an electron gun control coupled to the electron gun to selectively activate the electron gun and produce the electron beam traversing through the accelerator, the accelerator accelerating the electron beam to a therapeutic energy level;
a beam monitor downstream of the exit of the accelerator; and
a beam monitor interface coupled to the beam monitor, the beam monitor and beam monitor interface configured to measure and monitor absorbed dose delivered by the electron beam.

8. The intraoperative radiation therapy system of claim 1, wherein:
the robot assembly includes a robot controller to control movements of the robot assembly, and the at least one haptic control assembly comprises:
a force-torque sensor coupled to the treatment head, the robot controller in communication with the force-torque sensor; and
an elongate haptic handle mounted to the force-torque sensor, the haptic handle being moveable in 3-D space in response to user operation of the haptic handle, the force-torque sensor sensing the magnitude and direction of force and/or torque being applied to the haptic handle and generating data signals to be transmitted to the robot controller, thereby facilitating corollary translative movements of the treatment head and robot assembly in the general direction of user operation for coarse alignment of the treatment head.

9. The intraoperative radiation therapy system of claim 8, wherein the at least one haptic control assembly further comprises:
a motion-enable switch coupled to the haptic handle, wherein selective activation of the motion-enable switch permits the corollary translative movements to occur while the motion-enable switch is active and prevents the corollary translative movements from occurring when the motion-enable switch is inactive.

10. The intraoperative radiation therapy system of claim 1, wherein the controller comprises:
a main controller coupled to the cart and the robot assembly, the main controller controlling operations of the IORT system depending on input from the control panel and the haptic control assembly.

11. The intraoperative radiation therapy system of claim 1, wherein the plurality of switches for controlling movements on the control panel comprises:
a key switch configured to toggle the IORT system between an "OFF" mode, a cart mode, and a head/robot mode;
a motion-enable switch to enable selective movement of the cart and the robot assembly;
a joystick for driving or steering the cart while the motion-enable switch is active and the key switch is toggled to the cart mode;
a ready switch to place the robot assembly and the treatment head in a ready state, the ready state being assumed by concurrent activation of the motion-enable switch and the ready switch while the key switch is toggled to the head/robot mode;
a park switch to place the robot assembly and the treatment head in a parked state, the park state being assumed by concurrent activation of the motion-enable switch and the park switch while the key switch is toggled to the head/robot mode; and
an align switch to facilitate the autonomous fine alignment of the treatment head, the autonomous fine alignment being performed by concurrent activation of the motion-enable switch and the align switch while the key switch is toggled to the head/robot mode.

12. The intraoperative radiation therapy system of claim 1, further comprising:
a clamp assembly adapted to be detachably mounted to a bed of the patient, the clamp assembly configured to hold the at least one applicator in place during a treatment.

13. An intraoperative radiation therapy system, comprising:
a robot arm assembly comprising:
a plurality of arm members configured to provide a plurality of movement axes in the robot arm assembly to increase positional flexibility and reach of the robot arm assembly;
a rotary base configured to be mounted on a surface, the rotary base being selectively rotatable about a vertical first axis during positioning of the intraoperative radiation therapy system for a treatment; and
a radial section extending from the rotary base, the radial section having a first pivot joint at a distal end offset from the rotary base, the first pivot joint defining a horizontal second axis orthogonal to the first axis, at least one of the plurality of arm members being pivotally coupled to the first pivot joint;
a treatment head coupled to at least one arm member of the plurality of arm members of the robot arm assembly, the treatment head having a working end adapted to emit a therapeutic beam towards a target area for radiation therapy, the treatment head adapted to be aligned with an applicator adapted to be fixed near the target area of a patient, the applicator configured to shape the therapeutic beam from the treatment head to the target area for the treatment;

at least one sensor array coupled to the working end of the treatment head, the at least one sensor array having a plurality of sensors adapted to detect a surface on the applicator within a detection range and measure a relative distance to the detected surface;

at least one haptic control assembly coupled to the treatment head, the haptic control assembly configured to selectively move the plurality of arm members of the robot arm assembly to align in a coarse alignment the working end of the treatment head with an end of the applicator along an applicator axis to position the end of the applicator within the detection range of the at least one sensor array on the treatment head by selective operation of the at least one haptic control assembly; and a controller in communication with a control panel in the intraoperative radiation therapy system, the controller, based on input from the control panel, selectively controls the robot arm assembly and the treatment head after the coarse alignment to provide an autonomous fine alignment of the treatment head with the end of the applicator based on sensed data from the at least one sensor array.

14. The intraoperative radiation therapy system of claim 13, wherein the plurality of arm members comprises:

an elongate first arm member having one end pivotally coupled to the first pivot joint of the radial section to thereby selectively rotate about the second axis;

a second pivot joint disposed on the opposite end of the first arm member, the second pivot joint defining a third axis spaced and parallel to the second axis;

an elongate second arm member having one end pivotally coupled to the second pivot joint to thereby selectively rotate about the third axis, the coupling between the first arm member and the second arm member facilitating selective raising and lowering of the robot arm assembly within a vertical plane and thereby raise or lower the treatment head coupled to the at least one arm member of the robot arm assembly;

a third pivot joint disposed on the opposite end of the second arm member, the third pivot joint defining a fourth axis orthogonal to the second and third axes and coaxial with the second arm member;

an elongate third arm member having one end pivotally coupled to the third pivot joint, the third arm member being coaxial with the second arm member, the third pivot joint facilitating selective rotation of the third arm member about the fourth axis; and a combination joint assembly disposed at the opposite end of the third arm member, the treatment head being coupled to the combination joint assembly to facilitate positioning of the treatment head with respect to the second arm member, selective rotation of the third arm member facilitating selective oscillation of the treatment head about the fourth axis relative to the second arm member.

15. The intraoperative radiation therapy system of claim 14, wherein the combination joint assembly comprises:

a fourth pivot joint disposed on the opposite end of the third arm member, the fourth pivot joint defining a fifth axis orthogonal to the fourth axis, the fourth pivot joint facilitating selective forward and backward pitching of the treatment head about the fifth axis relative to the third arm member; and a fifth pivot joint operatively coupled to the fourth pivot joint, the fifth pivot joint defining a sixth axis orthogonal to the fifth axis, the fifth pivot joint facilitating selective rotation of the treatment head about the sixth axis.

16. The intraoperative radiation therapy system of claim 15, further comprising:

a moveable cart adapted for selective transport of the intraoperative radiation therapy system, wherein the robot arm assembly is coupled to the cart.

17. The intraoperative radiation therapy system of claim 13, further comprising:

a moveable cart adapted for selective transport of the intraoperative radiation therapy system, wherein the robot arm assembly is coupled to the cart.

18. The intraoperative radiation therapy system of claim 13, wherein:

the plurality of movement axes in the robot arm assembly comprises at least five movement axes for the plurality of arm members.

19. The intraoperative radiation therapy system of claim 13, wherein:

the plurality of sensors of the at least one sensor array comprises laser light optical sensors that detect the surface of the applicator and measure the relative distance to the detected surface of the applicator.

20. A method for intraoperative radiation therapy treatment, comprising the steps of:

providing an intraoperative radiation therapy treatment system including:

a robot assembly having at least one elongate arm and at least five movement axes to increase positional flexibility and reach;

at least one applicator adapted to be fixed near a target area of a patient, the at least one applicator having an elongate tube and an open endcap detachably mounted to one end of the tube, the at least one applicator defining an applicator axis;

a treatment head coupled to an elongate arm of the at least one elongate arm, the treatment head having a working end adapted to emit a therapeutic beam towards the target area for radiation therapy;

at least one haptic control assembly coupled to the treatment head, the haptic control assembly configured to move the treatment head for a coarse alignment within detection range of the endcap on the applicator;

a sensor array coupled to the working end of the treatment head, the sensor array having a plurality of sensors including axial alignment sensors and radial alignment sensors each with a given operational range, the axial alignment sensors and the radial alignment sensors adapted to detect surfaces on the endcap and measure relative distance therebetween; and a control panel having a plurality of switches in communication with a controller for controlling movements of the robot assembly and the treatment head;

operating the at least one haptic control assembly to move the treatment head into a coarse alignment position for the coarse alignment of the treatment head with respect to the endcap and within a sensing range of the sensor array;

sensing relative proximity between the endcap and the treatment head along a top surface and an outer surface of the endcap and generating relative proximity data therefrom;

determining axial alignment and radial alignment of the treatment head with respect to the endcap by comparing given dimensions of the endcap with the generated relative proximity data, mismatched proximity readings among the axial alignment sensors and among the radial alignment sensors indicating a misaligned condition of the treatment head; and performing automatic fine alignment of the treatment head by selective operation of the control panel in association with the controller to automatically manipulate the robot assembly and the treatment head until proximity data among the axial alignment sensors match with each other and proximity data among the radial alignment sensors match with each other.

21. The method for intraoperative radiation therapy treatment of claim 20, further comprising the steps of:

providing a moveable cart adapted for selective transport of the intraoperative radiation therapy treatment system, wherein the robot assembly is coupled to the cart; and controlling selective movement of the cart, the robot assembly and the treatment head by the control panel in communication with the controller.

22. An intraoperative radiation therapy system, comprising:

a moveable cart adapted for selective transport;

a robot assembly coupled to the cart, the robot assembly having at least one elongate arm and at least five movement axes to increase positional flexibility and reach;

at least one applicator adapted to be fixed near a target area of a patient, the at least one applicator having an elongate tube and an open endcap detachably mounted to one end of the tube, the at least one applicator defining an applicator axis;

a treatment head coupled to the at least one arm, the treatment head having a working end adapted to emit therapeutic beams towards the target area for radiation therapy, the treatment head adapted to be aligned with the applicator axis in a soft-docking process, wherein the working end of the treatment head comprises:
a faceplate; and
a central beam nozzle extending from the faceplate, the therapeutic beams exiting from the treatment head through the beam nozzle, the beam nozzle defining an axis for the therapeutic beams;

at least one haptic control assembly coupled to the treatment head, the haptic control assembly configured to move the treatment head for a coarse alignment within detection range of the endcap on the applicator;

a sensor array coupled to the working end of the treatment head, the sensor array having a plurality of sensors with a given operational range, the sensors adapted to detect surfaces on the endcap and measure relative distance therebetween, selective operation of the at least one haptic control assembly moving the sensor array within sensing range of the endcap for the coarse alignment; and a control panel associated with a controller having a plurality of switches for controlling movements of the cart, the robot assembly, and the treatment head, wherein after coarse alignment, selective operation of the control panel facilitates autonomous fine alignment of the treatment head based on sensed data from the sensor array.

23. The intraoperative radiation therapy system of claim 22, wherein the plurality of sensors comprises:

a first sensor set mounted to the working end of the treatment head, the first sensor set configured to sense proximity of a top surface of the endcap in an axial direction from the treatment head; and a second sensor set extending down from the working end of the treatment head, the second sensor set being outwardly spaced further from the first sensor set, the second sensor set configured to sense proximity of an outer surface of the endcap in a radial direction orthogonal to the axial direction.

24. The intraoperative radiation therapy system of claim 23, wherein the first sensor set comprises:

a plurality of axial alignment sensors, each axial alignment sensor configured to detect relative distance between the top surface of the endcap and the working end of the treatment head, wherein axial alignment between the applicator and the treatment head is achieved when each axial alignment sensor reads the same distance, and any substantive difference in read distance by the axial alignment sensors indicates misalignment requiring autonomous fine alignment.

25. The intraoperative radiation therapy system of claim 24, wherein:

the plurality of axial alignment sensors are arranged on the working end of the treatment head in a circular equidistant pattern about the axis of the beam nozzle to thereby form an inner ring of sensors.

26. The intraoperative radiation therapy system of claim 23, wherein the second sensor set comprises:

a plurality of radial sensor supports extending down from the working end of the treatment head; and a plurality of radial alignment sensors each mounted to a distal end of each radial sensor support, each radial alignment sensor configured to detect relative radial distance between the outer surface of the endcap and a respective radial alignment sensor of the plurality of radial alignment sensors, wherein radial alignment between the applicator and the treatment head is achieved when each radial alignment sensor reads the same distance, and any substantive difference in read distance by the radial alignment sensors indicates misalignment requiring autonomous fine alignment.

27. The intraoperative radiation therapy system of claim 26, wherein:

the plurality of radial alignment sensors are arranged on the working end of the treatment head in a circular equidistant pattern about the axis of the beam nozzle to thereby form an outer ring of sensors.

28. The intraoperative radiation therapy system of claim 26, further comprising:

at least one indicator light mounted to each radial sensor support, the at least one indicator light configured to activate based upon a sensed condition from the plurality of sensors.

29. The intraoperative radiation therapy system of claim 23, wherein:

the first sensor set and the second sensor set comprise laser light optical sensors.

30. An intraoperative radiation therapy system, comprising:
- a robot arm assembly having a plurality of arm members configured to provide a plurality of movement axes in the robot arm assembly to increase positional flexibility and reach of the robot arm assembly;
- a treatment head coupled to at least one arm member of the plurality of arm members of the robot arm assembly, the treatment head having a working end adapted to emit a therapeutic beam towards a target area for radiation therapy, the treatment head adapted to be aligned with an applicator adapted to be fixed near the target area of a patient, the applicator configured to shape the therapeutic beam from the treatment head to the target area for a treatment;
- at least one sensor array coupled to the working end of the treatment head, the at least one sensor array having a plurality of sensors adapted to detect a surface on the applicator within a detection range and measure a relative distance to the detected surface;
- at least one haptic control assembly coupled to the treatment head, the haptic control assembly configured to selectively move the plurality of arm members of the robot arm assembly to align in a coarse alignment the working end of the treatment head with an end of the applicator along an applicator axis to position the end of the applicator within the detection range of the at least one sensor array on the treatment head by selective operation of the at least one haptic control assembly; and
- a controller in communication with a control panel in the intraoperative radiation therapy system, the controller, based on input from the control panel, selectively controls the robot arm assembly and the treatment head after the coarse alignment to provide an autonomous fine alignment of the treatment head with the end of the applicator based on sensed data from the at least one sensor array,
- wherein the at least one sensor array senses predetermined features of a top surface and an outer surface of an endcap of the applicator to provide the sensed data for at least one of the coarse alignment or the autonomous fine alignment of the treatment head.

31. An intraoperative radiation therapy system, comprising:
- a robot arm assembly having a plurality of arm members configured to provide a plurality of movement axes in the robot arm assembly to increase positional flexibility and reach of the robot arm assembly;
- a treatment head coupled to at least one arm member of the plurality of arm members of the robot arm assembly, the treatment head having a working end adapted to emit a therapeutic beam towards a target area for radiation therapy, the treatment head adapted to be aligned with an applicator adapted to be fixed near the target area of a patient, the applicator configured to shape the therapeutic beam from the treatment head to the target area for a treatment;
- at least one sensor array coupled to the working end of the treatment head, the at least one sensor array having a plurality of sensors adapted to detect a surface on the applicator within a detection range and measure a relative distance to the detected surface;
- at least one haptic control assembly coupled to the treatment head, the haptic control assembly configured to selectively move the plurality of arm members of the robot arm assembly to align in a coarse alignment the working end of the treatment head with an end of the applicator along an applicator axis to position the end of the applicator within the detection range of the at least one sensor array on the treatment head by selective operation of the at least one haptic control assembly; and
- a controller in communication with a control panel in the intraoperative radiation therapy system, the controller, based on input from the control panel, selectively controls the robot arm assembly and the treatment head after the coarse alignment to provide an autonomous fine alignment of the treatment head with the end of the applicator based on sensed data from the at least one sensor array,
- wherein the at least one sensor array comprises a plurality of proximity sensors divided into a first sensor set for detecting predetermined features of a top surface of an endcap of the applicator and a second sensor set for detecting predetermined features of an outer surface of the endcap of the applicator to provide the sensed data for at least one of the coarse alignment or the autonomous fine alignment of the treatment head.

32. An intraoperative radiation therapy system, comprising:
- a robot arm assembly having a plurality of arm members configured to provide a plurality of movement axes in the robot arm assembly to increase positional flexibility and reach of the robot arm assembly;
- a treatment head coupled to at least one arm member of the plurality of arm members of the robot arm assembly, the treatment head having a working end adapted to emit a therapeutic beam towards a target area for radiation therapy, the treatment head adapted to be aligned with an applicator adapted to be fixed near the target area of a patient, the applicator configured to shape the therapeutic beam from the treatment head to the target area for a treatment;
- at least one sensor array coupled to the working end of the treatment head, the at least one sensor array having a plurality of sensors adapted to detect a surface on the applicator within a detection range and measure a relative distance to the detected surface;
- at least one haptic control assembly coupled to the treatment head, the haptic control assembly configured to selectively move the plurality of arm members of the robot arm assembly to align in a coarse alignment the working end of the treatment head with an end of the applicator along an applicator axis to position the end of the applicator within the detection range of the at least one sensor array on the treatment head by selective operation of the at least one haptic control assembly; and
- a controller in communication with a control panel in the intraoperative radiation therapy system, the controller, based on input from the control panel, selectively controls the robot arm assembly and the treatment head after the coarse alignment to provide an autonomous fine alignment of the treatment head with the end of the applicator based on sensed data from the at least one sensor array,
- wherein the at least one sensor array comprises a plurality of proximity sensors divided into a first sensor set of axial alignment sensors for detecting predetermined features of a top surface of an endcap of the applicator and a second sensor set of radial alignment sensors for detecting predetermined features of an outer surface of the endcap of the applicator to provide the sensed data for at least one of the coarse alignment or the autonomous fine alignment of the treatment head.

33. An intraoperative radiation therapy system, comprising:
- a robot arm assembly having a plurality of arm members configured to provide a plurality of movement axes in the robot arm assembly to increase positional flexibility and reach of the robot arm assembly;
- a treatment head coupled to at least one arm member of the plurality of arm members of the robot arm assembly, the treatment head having a working end adapted to emit a therapeutic beam towards a target area for radiation therapy, the treatment head adapted to be aligned with an applicator adapted to be fixed near the target area of a patient, the applicator configured to shape the therapeutic beam from the treatment head to the target area for a treatment, wherein the applicator comprises:
  - a tube; and
  - an open endcap mounted to one end of the tube, the endcap having a predetermined outer diameter and an axial length, the outer diameter of the endcap defining an outer cylindrical surface along the axial length and a top of the endcap defining an annular planar top surface, the endcap having a center bore, the center bore having a diameter substantially the same as a diameter of a beam nozzle on the working end of the treatment head that communicates with the center bore of the endcap;
- at least one sensor array coupled to the working end of the treatment head, the at least one sensor array having a plurality of sensors adapted to detect a surface on the applicator within a detection range and measure a relative distance to the detected surface;
- at least one haptic control assembly coupled to the treatment head, the haptic control assembly configured to selectively move the plurality of arm members of the robot arm assembly to align in a coarse alignment the working end of the treatment head with an end of the applicator along an applicator axis to position the end of the applicator within the detection range of the at least one sensor array on the treatment head by selective operation of the at least one haptic control assembly; and
- a controller in communication with a control panel in the intraoperative radiation therapy system, the controller, based on input from the control panel, selectively controls the robot arm assembly and the treatment head after the coarse alignment to provide an autonomous fine alignment of the treatment head with the end of the applicator based on sensed data from the at least one sensor array.

34. The intraoperative radiation therapy system of claim 33, wherein:
- the outer diameter of the endcap is greater than an outer diameter of the tube to provide a buffer to prevent the therapeutic beam from reaching the patient by travelling alongside the tube, and
- the tube shapes the therapeutic beam into a form suitable for the treatment and defines a guided passageway for traversal of the therapeutic beam.

35. The intraoperative radiation therapy system of claim 33, wherein the at least one sensor array comprises:
- a plurality of proximity sensors divided into a first sensor set of axial alignment sensors for detecting predetermined features of the annular planar top surface of the endcap of the applicator and a second sensor set of radial alignment sensors for detecting predetermined features of the outer cylindrical surface of the endcap of the applicator to provide the sensed data for at least one of the coarse alignment or the autonomous fine alignment of the treatment head.

\* \* \* \* \*